United States Patent [19]

Plow et al.

[11] Patent Number: 5,262,520
[45] Date of Patent: * Nov. 16, 1993

[54] PEPTIDES AND ANTIBODIES THAT INHIBIT INTEGRIN-LIGAND BINDING

[75] Inventors: Edward F. Plow; Stanley E. D'Souza; Mark H. Ginsberg, all of San Diego, Calif.

[73] Assignee: The Scripps Research Institute, La Jolla, Calif.

[*] Notice: The portion of the term of this patent subsequent to Mar. 23, 2010 has been disclaimed.

[21] Appl. No.: 620,823

[22] Filed: Nov. 29, 1990

Related U.S. Application Data

[63] Continuation-in-part of Ser. No. 444,777, Dec. 1, 1989, Pat. No. 5,196,511.

[51] Int. Cl.$^5$ .................... C07K 07/08; C07K 07/10
[52] U.S. Cl. .................... 530/326; 530/324; 530/325; 530/327; 530/328; 530/388.2; 530/389.1; 536/23.5
[58] Field of Search .............................. 530/324-328, 530/387, 788.2, 389.1; 536/27, 23.5

[56] References Cited

PUBLICATIONS

Dane et al. "Two Functional Domains in the Phagocyte Membrane . . . " J. of Immunology v. 137, pp. 3259–3263, Nov. 15, 1986.

Hildreth et al. "The Human Lymphocyte Function-Associated . . . " Journal of Immunology v. 134, pp. 3272–3280, May 1985.

Corbi et al. "the Human Leukocyte Adhesion Colycoprotein MAC-1 . . . " J. Biol. Chemistry, v. 263 (25), pp. 12403–12411, Sep. 5, 1988.

Mehra et al. "Efficient Mapping of Protein Antigenic Determinants" Proc. Natl. Acad. Sci. U.S.A. vol. 83, pp. 7013–7017, Sep. 1986.

*Primary Examiner*—Nina Ossanna
*Attorney, Agent, or Firm*—Douglas A. Bingham; Thomas Fitting; April C. Logan

[57] ABSTRACT

Polypeptides derived from the ligand-binding portion of an Integrin alpha subunit are disclosed as are their use for modulation of Integrin ligand binding. Anti-peptide antibodies, hybridomas secreting the antibodies, as well as methods of making and using such antibodies and recombinant DNA molecules coding for the polypeptides are also described. The polypeptides and antibodies to the polypeptides are effective inhibitors of fibrinogen binding to platelets.

8 Claims, 14 Drawing Sheets

FIG. 1-1

```
                                                                              -16
  1   GATGGCCAGAGCTTTGTGTCCACTGCAAGCCCCTCTGGCTTCTGGAGTG
       M  A  R  A  L  C  P  L  Q  A  L  W  L  L  E  W 1
 49   GGTGCTGCTGCTCTTGGGACCTTGTGCTGCCCCTCCAGCCTGGGCCTT
       V  L  L  L  L  G  P  C  A  A  P  P  A  W  A  L 17
 97   GAACCTGGACCCAGTGCAGCTCACCTTCTATGCAGGCCCCAATGGCAG
       N  L  D  P  V  Q  L  T  F  Y  A  G  P  N  G  S 33
145   CCAGTTTGGATTTTCACTGGACTTCCACAAGGACAGCCATGGGAGAGT
       Q  F  G  F  S  L  D  F  H  K  D  S  H  G  R  V 49
193   GGCCATCGTGGTGGGCGCCCCCCGCACCCTGGGCCCCAGCCAGGAGGA
       A  I  V  V  G  A  P  R  T  L  G  P  S  Q  E  E 65
241   GACGGGGGCGTGTTCCTGTGCCCCTGGAGGGCGGCCGAGGGGCAGTG
       T  G  G  V  F  L  C  P  W  R  A  E  G  G  Q  C 81
289   CCCCTCGCTGCTCTTTGACCTCCGTGATGAGACCCGAAATGTAGGCTC
       P  S  L  L  F  D  L  R  D  E  T  R  N  V  G  S 97
337   CCAAACTTTACAAACCTTCAAGGCCCGCCAAGGACTGGGGGCGTCGGT
       Q  T  L  Q  T  F  K  A  R  Q  G  L  G  A  S  V
```

FIG. 1-2

```
385  CGTCAGCTGGAGGCGGACGTCATTGTGGCCTGGCCCCCTGGCAGCACTG   113
      V  S  W  S  D  V  I  V  A  C  A  P  W  Q  H  W
433  GAACGTCCTAGAAAAGACTGAGGAGGCTGAGAAGACGCCCGTAGGTAG    129
      N  V  L  E  K  T  E  E  A  E  K  T  P  V  G  S
481  CTGCTTTTTGGCTCAGCCAGAGAGCGGCCGCCGAGTACTCCCC        145
      C  F  L  A  Q  P  E  S  G  R  R  A  E  Y  S  P
529  CTGTCGCGGGAACACCCTGAGCCGCATTTACGTGGAAAATGATTTTAG   161
      C  R  G  N  T  L  S  R  I  Y  V  E  N  D  F  S
577  CTGGGACAAGCGTTACTGTGAAGCGGCTTCAGCTCGGTGGTCACTCA    177
      W  D  K  R  Y  C  E  A  G  F  S  S  V  V  T  Q
625  GGCCGGAGAGCTGGTGCTTGGGGCCGGAGCTGTCCTATTATTCTTAGG   193
      A  G  E  L  V  L  G  A  P  G  G  Y  Y  F  L  G
673  TCTCCTGGCCCAGGCTCCAGTTGCGGATATTTTCTGAGTTACCGCCC    209
      L  L  A  Q  A  P  V  A  D  I  F  S  S  Y  R  P
721  AGGCATCCTTTTGTGGCACGTGTCCTCCCCAGAGCCTCTCCTTTGACTC  225
      G  I  L  L  W  H  V  S  S  Q  S  L  S  F  D  S
```

FIG. 1-3

```
 769  CAGCAACCCAGAGTACTTCGACGGCTACTGGGGTACTCGGTGGCCGT   241
        S   N   P   E   Y   F   D   G   Y   W   G   Y   S   V   A   V

817  GGGCGAGTTCGACGGGGATCTCAACACTACAGAATATGTCGTCGGTGC   257
        G   E   F   D   G   D   L   N   T   T   E   Y   V   V   G   A

865  CCCCACTTGGAGCTGGACCCTGGGAGCGGTGGAAATTTTGGATTCCTA   273
        P   T   W   S   W   T   L   G   A   V   E   I   L   D   S   Y

913  CTACCAGAGGCTGCATCGGCTGCGCGCAGAGCAGATGGCGTCGTATTT   289
        Y   Q   R   L   H   R   L   R   G   E   Q   M   A   S   Y   F

961  TGGGCATTCAGTCGCTGTCACTGACGTCAACGGGGATGGGAGGCATGA   305
        G   H   S   V   A   V   T   D   V   N   G   D   G   R   H   D

1009  TCTGCTGGTGGGCGCTCCACTGTATATGGAACAGCCGGCAGACCGAAA   321
        L   L   V   G   A   P   L   Y   M   E   S   R   A   D   R   K

1057  ACTGGCCGAAGTGGGGCGTGTGTATTTGTTCCTGCAGCCGCCAGGCCC   337
        L   A   E   V   G   R   V   Y   L   F   L   Q   P   R   G   P

1105  CCACGCGCTGGGTGCCCCCAGCCTCCTGCTGACTGGCACACAGCTCTA   353
        H   A   L   G   A   P   S   L   L   L   T   G   T   Q   L   Y
```

FIG. 1-4

```
1153  TGGGCGATTCGGCTCTGCTGCCATCGCACCCCTGGGCGACCTCGACCGGGA   369
      G   R   F   G   S   A   I   A   P   L   G   D   L   D   R   D

1201  TGGCTACAATGACATTGCAGTGGCTGCCCCCTACGGGGGTCCCAGTGG      385
      G   Y   N   D   I   A   V   A   A   P   Y   G   G   P   S   G

1249  CCGGGGCCAAGTGCTGGTGTTCCTGGGTCAGAGTGAGGGCTGAGGTC       401
      R   G   Q   V   L   V   F   L   G   Q   S   E   G   L   R   S

1297  ACGTCCCTCCCAGGTCCTGGACAGCCCCTTCCCCACAGGCTCTGCCTT      417
      R   P   S   Q   V   L   D   S   P   F   P   T   G   S   A   F

1345  TGGCTTCTCCCTTCGAGGTGCCGTAGACATGACAACGGATACCC         433
      G   F   S   L   R   G   A   V   D   I   D   D   N   G   Y   P

1393  AGACCTGATCGTGGGAGCTTACGGGGCCAACCAGGTGGCTGTGTACAG      449
      D   L   I   V   G   A   Y   G   A   N   Q   V   A   V   Y   R

1441  AGCTCAGCCAGTGGTGAAGGCCTCTGTCCAGCTACTGGTGCAAGATTC      465
      A   Q   P   V   V   K   A   S   V   Q   L   L   V   Q   D   S

1489  ACTGAATCCTGCTGTGAAGAGCTGTGTCCTACCTCAGACCAAGACACC      481
      L   N   P   A   V   K   S   C   V   L   P   Q   T   K   T   P
```

FIG. 1-5

```
1537  CGTGAGCTGCTTCAACATCCAGATGTGTGTTGGAGCCACTGGGCACAA   497
       V  S  C  F  N  I  Q  M  C  V  G  A  T  G  H  N

1585  CATTCCTCAGAAGCTATCCCTAAATGCCGAGCTGCAGCTGGACCGGCA   513
       I  P  Q  K  L  S  L  N  A  E  L  Q  L  D  R  Q

1633  GAAGCCCCGCCAGGGCCGGGGTGCTGCTGGGCTCTCAACAGGC        529
       K  P  R  Q  G  R  R  V  L  L  G  S  Q  Q  A

1681  AGGCACCACCCTGAACCTGGATCTGGGCGGAAAGCACAGCCCCATCTG   545
       G  T  T  L  N  L  D  L  G  G  K  H  S  P  I  C

1729  CCACACCACCATGGCCTTCCTTCGAGATGAGGCAGACTTCCGGGACAA   561
       H  T  T  M  A  F  L  R  D  E  A  D  F  R  D  K

1777  GCTGAGCCCCATTGTGCTCAGCCTCAATGTCCCTACCGCCACGGA      577
       L  S  P  I  V  L  S  L  N  V  S  L  P  P  T  E

1825  GGCTGGAATGGCCCCTGCTGTCGTGCTGCATGGAGACACCCATGTGCA   593
       A  G  M  A  P  A  V  V  L  H  G  D  T  H  V  Q

1873  GGAGCAGACACGAATCGTCCTGGACTCTGGGGAAGATGACGTATGTGT   609
       E  Q  T  R  I  V  L  D  S  G  E  D  D  V  C  V
```

FIG. 1-6

```
1921  GCCCCAGCTTCAGCTCACTGCCAGCGTGACGGGCTCCCCGCTCCTAGT   625
       P  Q  L  Q  L  T  A  S  V  T  G  S  P  L  L  V

1969  TGGGGCAGATAATGTCCTGGAGCTGCAGATGGACGCAGCCAACGAGGG   641
       G  A  D  N  V  L  E  L  Q  M  D  A  A  N  E  G

2017  CGAGGGGCCTATGAAGCAGAGCTGGCGGTGCACCTGCCCCAGGGCGC   657
       E  G  A  Y  E  A  E  L  A  V  H  L  P  Q  G  A

2065  CCACTACATGCGGGCCCTAAGCAATGTCGAGGGCTTTGAGAGACTCAT   673
       H  Y  M  R  A  L  S  N  V  E  G  F  E  R  L  I

2113  CTGTAATCAGAAGAAGGAGAATGAGACCAGGGTGGTCTGTGTGAGCT   689
       C  N  Q  K  K  E  N  E  T  R  V  V  L  C  E  L

2161  GGGCAACCCCATGAAGAAGAACGCCCAGATAGGAATCGCGATGTTGGT   705
       G  N  P  M  K  K  N  A  Q  I  G  I  A  M  L  V

2209  GAGCGTGGGGAATCTGGAAGAGGCTGGGGAGTCTGTGTCCTTCCAGCT   721
       S  V  G  N  L  E  E  A  G  E  S  V  S  F  Q  L

2257  GCAGATACGGAGCAAGAACAGCCAGAATCCAAACAGCAAGATTGTGCT   737
       Q  I  R  S  K  N  S  Q  N  P  N  S  K  I  V  L
```

FIG. 1-7

```
2305  GCTGGACGTGCCGGTCCGGGCAGAGGCCCAAGTGGAGCTGCGAGGAA  753
       L  D  V  P  V  R  A  E  A  Q  V  E  L  R  G  N
2353  CTCCTTTCCAGCCTCCCTGGTGGCAGCAGCAGAAGAAGGTGAGAGGA  769
       S  F  P  A  S  L  V  V  A  A  E  E  G  E  R  E
2401  GCAGAACAGCTTGGACAGCTGGGGACCCAAAGTGGAGCACACCTATGA  785
       Q  N  S  L  D  S  W  G  P  K  V  E  H  T  Y  E
2449  GCTCCACACAATGGCCCTGGAACTGTGAATGGTCTTCACCTCAGCAT  801
       L  H  N  N  G  P  G  T  V  N  G  L  H  L  S  I
2497  CCACCTTCCGGGACAGTCCCAGCCCCTCCGACCTGCTCTACATCCTGGA  817
       H  L  P  G  Q  S  Q  P  S  D  L  L  Y  I  L  D
2545  TATACAGCCCCAGGGGGCCTTCAGTGCTTCCCACAGCCTCCTGTCAA  833
       I  Q  P  Q  G  G  L  Q  C  F  P  Q  P  P  V  N
2593  CCCTCTCAAGGTGGACTGGGGCTGCCCATCCCCAGCCCCTCCCCCAT  849
       P  L  K  V  D  W  G  L  P  I  P  S  S  P  P  I
2641  TCACCCGGCCCATCACAAGCGGGATCGCAGAGACAGATCTTCCTGCCAGA  865
       H  P  A  H  H  K  R  D  R  R  Q  I  F  L  P  E
```

FIG. 1-8

```
2689  GCCCGAGCAGCCCTCGAGGCTTCAGGATCCAGTTCTCGTAAGCTGCGA  881
       P  E  Q  P  S  R  L  Q  D  P  V  L  V  S  C  D
2737  CTCGGGCGCCCTGTACTGTGGTGCAGTGTGACCTGCAGGAGATGGCGCG  897
       S  A  P  C  T  V  V  Q  C  D  L  Q  E  M  A  R
2785  CGGGCAGCGGGCCATGGTGACGGTCACGGTGCTGGCCTTCCTGTGGCCAG  913
       G  Q  R  A  M  V  T  V  L  A  F  L  W  L  P  S
2833  CCTCTACCAGAGGCCCTCTGGATCAGTTTGTGCTGCAGTCGCACGCATG  929
       L  Y  Q  R  P  L  D  Q  F  V  L  Q  S  H  A  W
2881  GTTCAACGTGTCCTCCCTCCCCTATGCGGTTGTGCCCCCGCTCAGCCTGCC  945
       F  N  V  S  S  L  P  Y  A  V  P  P  L  S  L  P
2929  CCGAGGGGAAGCTCAGGTGTGGACACAGCTGCTCCGGGCCTTGGAGGA  961
       R  G  E  A  Q  V  W  T  Q  L  L  R  A  L  E  E
2977  GAGGGCCATTCCAATCTGGTGGCTGGGTGTGCTGGGTGTGCTGGGGTGGCCT  977
       R  A  I  P  I  W  W  V  L  V  G  V  L  G  G  L
```

FIG. 1-9

```
3025  GCTGCTGCTCACCATCCTGGTCCTGGCCATGTGGAAGGTCGGCTTCTT
       L  L  L  T  I  L  V  L  A  M  W  K  V  G  F  F   993
3073  CAAGCGGAACCGGCCACCCCTGGAAGAAGATGATGAAGAGGGGAGTG
       K  R  N  R  P  P  L  E  E  D  D  E  E  G  E     1008
3121  ATGGTGCAGCCTACACTATTCTAGCAGGAGGGTTGGGGCGTGCTACCTG
3169  CACC
```

FIG. 2A    FIG. 2B    FIG. 2C
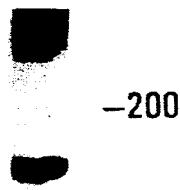
FIG. 3

CNBr: L N L D P V Q L T F Y A G P

Chymotrypsin: A V T D V N

V8: Y X V G A P T X X W T L G A V E

PEPTIDES AND ANTIBODIES THAT INHIBIT INTEGRIN-LIGAND BINDING

This invention was made with government support under National Institutes of Health Contracts HL 16411 and HL 38292. The government has certain rights in the invention.

CROSS-REFERENCE TO RELATED APPLICATION

The present application is a continuation-in-part of copending application Ser. No. 444,777, filed Dec. 1, 1989, now U.S. Pat. No. 5,196,511, which disclosure is herein incorporated by reference.

TECHNICAL FIELD

The present invention relates to polypeptides derived from the ligand-binding region of Integrin alpha subunits and to use of the polypeptides to modulate Integrin-ligand binding. Also contemplated are antibodies that immunoreact with the ligand-binding region of an Integrin alpha subunit and use of the antibodies to modulate or detect Integrin-ligand binding or detect ligand binding sites within Integrins.

BACKGROUND

Cell adhesion generally involves recognition of specific adhesive proteins by cell surface receptors. A family of cell surface receptors of particular interest to the present invention are the Integrins.

According to Hynes, Cell, 48:549–554 (1987), Integrins are a functionally and structurally related group of receptors that interact with a wide variety of ligands including extracellular matrix glycoproteins, complement and other cells. Integrins participate in cell-matrix and cell-cell adhesion in many physiologically important processes including embryological development, hemostasis, thrombosis, wound healing, immune and nonimmune defense mechanisms and oncogenic transformation. At least two human genetic diseases, Glanzmann's thrombasthenia and leukocyte adhesion deficiency, involve members of the Integrin family.

Structurally, Integrins are heterodimeric complexes comprised of noncovalently associated alpha and beta subunits. Within the Integrin family there are recognized subfamilies related by the presence of a similar beta subunit and members within each group are distinguished by distinct alpha subunits.

For instance, recent evidence indicates that an Integrin found on the surface of platelets and known as GPIIb-IIIa is one of several adhesion receptors that have distinct alpha subunits but share a similar beta subunit and the functional property of recognizing the tripeptide amino acid residue sequence Arg-Gly-Asp (using single letter symbols, RGD). Pytela et al., Science, 231:1559–1562 (1986) and Ruoslahti et al., Cell, 44:517–518 (1986). In addition to GPIIb-IIIa, this group of related receptors includes the vitronectin receptor (VnR) and fibronectin receptor (FnR) isolated from osteosarcoma cells. Pytela et al., Cell, 40:191–198 (1985), and Pytela et al., Proc. Natl. Acad. Sci. USA, 82:5766–5770 (1985).

The similar functional, structural, and antigenic properties of these proteins suggests GPIIb-IIIa and VnR are members of an Integrin subfamily for which the designation "cytoadhesin" has been proposed. Plow et al., Proc. Natl. Acad. Sci. USA. 83:6002–6006 (1986).

Within the cytoadhesin group, distinct alpha subunits combine with a common or very similar beta subunit, resulting in functionally distinguishable receptors. Ginsberg et al., J. Biol. Chem., 262:5437–5440 (1987).

For example, GPIIb-IIIa is a heterodimer complex comprised of alpha and beta subunits. Jennings et al., J. Biol. Chem., 257:10458–10466 (1982). The alpha subunit, GPIIb, consists of a heavy chain and a light chain that are linked together by disulfide bonds. The beta subunit, GPIIIa is a single chain polypeptide of about 100 kDa. Phillips et al., J. Biol. Chem., 252:2121–2126 (1977). Cell surface molecules immunologically related to GPIIb-IIIa have been identified on a variety of cell types. See Thiagarajan et al., J. Clin. Invest., 75:896–901 (1985); Plow et al., Proc. Natl. Acad. Sci. USA. 83:6002–6006 (1986); and Fitzgerald et al., J. Biol. Chem., 260:10893–10896 (1985).

GPIIb-IIIa contributes to platelet function through interactions with RGD-containing proteins, i.e., proteins containing an Arg-Gly-Asp amino acid residue sequence, such as fibrinogen [Bennett et al., Proc. Natl. Acad. Sci. USA, 80:2417–2421 (1983)], fibronectin [Ginsberg et al., J. Clin. Invest., 71:619–624 (1983)], and von Willebrand factor [Ruggeri et al., Proc. Natl. Acad. Sci. USA, 79:6038–6041 (1982)], and therefore is a component of the common platelet adhesive protein receptor [Pytela et al., Science, 231:1559–1562 (1986) and Plow et al., J. Biol. Chem., 259:5388–5391 (1984)].

At least 2 other groups of heterodimeric adhesion receptors have been identified in which a common beta subunit combines with a number of distinct alpha subunits. One group is found on leukocytes and has been referred to as the leukocyte adhesion (LeuCam) family and includes LFA-1, Mac-1, and P150,95. Sanchez-Madrid et al., J. Exp. Med., 158:1785–1803 (1983) and Springer et al., Ciba. Found. Symp., 118:102–126 (1986). The other group is more widely distributed and has been referred to as the VLA family. Hemler et al., J. Biol. Chem., 262:3300–3309 (1987). The beta subunit of the VLA family [Hemler et al., J. Biol. Chem., 262:3300–3309 (1987)] in the chicken has been cloned, sequenced and designated "Integrin" [Tamkun et al., Cell, 46:271–282 (1986)]. The sequence of chicken Integrin is similar to that of GPIIIa [Fitzgerald et al., J. Biol. Chem., 262:3936–3939 (1987)] and to the beta subunit of the leukocyte adhesion family [Kishimoto et al., Cell, 48:681–690 (1987)]. Moreover, partial sequences of several alpha subunits also indicate similarities. Ginsberg, et al., J. Biol. Chem., 262:5437–5440 (1987); Suzuki, et al., Proc. Natl. Acad. Sci. USA, 83:8614–8618 (1986); and Charo, et al., Proc. Natl. Acad. Sci. USA, 83:8351–8356 (1986).

The sites on GPIIb-IIIa, or the other cytoadhesins, that are crucial for their functions as adhesion receptors are not presently well characterized. Several observations suggest that a functionally significant site on GPIIb-IIIa is near the epitope defined by the monoclonal antibody PMI-1. This antibody binds to the heavy chain of GPIIb [Shadle et al., J. Cell. Biol., 99:2056–2060 (1984)] and defines a region of GPIIb that is associated with several distinct functional activities. For instance, PMI-1 inhibits adhesion of washed platelets to collagen. Shadle et al., J. Cell. Biol., 99:2056–2060 (1984).

Recently, the site on the GPIIIa subunit for interaction with the RGD-containing region of fibrinogen was localized to residues 109–171 of GPIIIa by chemical crosslinking between GPIIIa and the synthetic polypeptide KYGRGDS. D'Souza et al., *Science*, 242:91-93 (1988). Studies to identify the site of interaction between fibrinogen gamma chain polypeptides and GPIIb-IIIa have shown an interaction with the GPIIb subunit. Kloczewick, M., et al., *J. Biochem.*, 23:1767-74 (1984). Only recently have peptides containing the gamma chain of fibrinogen been selectively crosslinked to an identifiable region, residues 294-314, of GPIIb. D'Souza, S. E., et al., *J. Biol. Chem.*, 265:3440-46 (1990). These results suggest a proximal relationship between the 294-314 residue region and the ligand binding site of GPIIb-IIIa.

BRIEF SUMMARY OF THE INVENTION

A newly characterized region of an Integrin alpha subunit has been identified that participates in ligand binding. More particularly, a new region of the GPIIb subunit of the platelet receptor glycoprotein, GPIIb-IIIa, has been identified that participates in the specific binding of GPIIb-IIIa to fibrinogen.

The invention relates to polypeptides [herein also referred to as subject polypeptide(s)] of about 10 to about 100 amino acid residues in length which are characterized as having an amino acid residue sequence substantially homologous to a portion of the ligand-binding region of an Integrin alpha subunit.

The invention also relates to polyclonal and monoclonal antibodies that immunoreact with a subject polypeptide as well as monoclonal antibodies that immunoreact with an epitope formed by the ligand-binding region of an Integrin alpha subunit. Such antibodies are effective in modulating the binding of fibrinogen to platelets.

Also contemplated within the scope of the present invention are the hybridomas having the capacity to produce a subject monoclonal antibody.

Methods are contemplated for modulating the adhesion, in vivo, of cells expressing an Integrin alpha subunit to which the subject polypeptides correspond. In this method cell adhesion is modulated using either the polypeptides or antipolypeptide antibodies of the present invention. Thus, platelet aggregation and platelet binding to fibrinogen may be inhibited.

Further contemplated is a nucleotide segment comprising no more than about 12,000 nucleotide base pairs including a sequence defining a structural gene coding for a subject polypeptide. Also contemplated is a recombinant DNA molecule comprising a vector operatively linked to a DNA segment that defines a structural gene coding for a subject polypeptide.

BRIEF DESCRIPTION OF THE DRAWINGS

In the drawings forming a portion of this disclosure:

FIGS. 1-1 through 1-9 illustrates (A and B) the nucleotide base sequence and deduced amino acid residue sequence of a DNA segment coding for the alpha subunit of GPIIb. Amino acid residues are indicated by the single letter code and are numbered sequentially in the right margin, beginning at −31 for the first methionine (M), and beginning at 1 for the first leucine (L) found on the protein after the 31 amino acid residue leader sequence is removed. Thus the GPIIb alpha subunit contains 1039 residues prior to cleavage of the leader sequence, and 1008 residues after cleavage of the leader from the amino terminus. Nucleic acid base residues are indicated by a single letter code, and are numbered sequentially in the left margin. The sequence shown is from the sequence of GPIIb reported by Poncz et al., *J. Biol. Chem.*, 262: 8476-82 (1987).

FIGS. 1-1 through 1-5 show the amino terminal half of GPIIb from am acid residue −31 to 508.

FIGS. 1-5 through 1-9 show the carboxy terminal half of GPIIb from amino acid residue 509 to 1008.

FIGS. 2A through 2C illustrate the results of crosslinking the gamma chain peptide (K16) to discrete sites in the alpha subunit (GPIIb) of an Integrin adhesion receptor. The $^{125}$I-labeled peptide, K16 (30 µM), was bound to platelet ($6 \times 10^8$/ml) for 45 min at 22° C., and crosslinked with $BS^3$ (0.2 mM) according to Example 1B. The crosslinked samples were analyzed by SDS-PAGE [Laemmli, *Nature*, 227:680 (1970)] and autoradiography according to Example 1B and 1C.

FIG. 2A shows the results of crosslinking $^{125}$I-K16 to thrombin stimulated platelets in the absence of peptide inhibitor (left lane) or in the presence of a 50-fold molar excess of unlabeled K16 peptide (right lane) as a control for crosslinking specificity.

FIG. 2B shows the results of an analysis by SDS-PAGE of the crosslinked samples after immunoprecipitation using the GPIIb heavy chain specific antibody, PMI-1.

FIG. 2C shows the results of an analysis by SDS-PAGE of the crosslinked samples prepared using platelets in the presence (lanes 2-4) of ADP (10 uM), PMA (0.1 uM) or thrombin (0.5 units/ml) and in the absence of agonists (lane 1).

FIG. 3 illustrates that the K16 crosslinking site resides in the heavy chain portion of the alpha subunit (GPIIb) according to Example 1C. $^{125}$I-K16 was first crosslinked to platelets. The crosslinked samples were then analysed by SDS-PAGE under non-reducing conditions, and the radioactive bands were excised and re-analysed on 10-20% gradient SDS-PAGE gels in the presence of 2-mercaptethanol. The resulting gels were subjected to immunoblot analysis according to Example 1C using an antibody that immunoreacts with the GPIIb heavy chain (lane 1) or the GPIIb light chain (lane 2). Lanes 3 and 4 show the autoradiogram of the extracted samples analysed on a second gel under non-reducing (lane 3) or reducing conditions (lane 4).

FIG. 4 illustrates localization of the K16 crosslinking site to the NHz-terminal region of the alpha subunit (GPIIb) according to Example ID. GPIIb heavy chain: K16 complex that was extracted from reducing SDS-PAGE gels as in FIG. 3 was digested with chymotrypsin, and then re-analysed by immunoblotting with a GPIIb heavy chain specific antibody, PMI-1 (lanes 1 and 2) or by autoradiography (lanes 3 and 4) according to Example 1D. Lanes 1 and 3 show the extracted complex without digestion, and lanes 2 and 4 show the extracted complex after digestion with chymotrypsin. The arrow indicates the position of the detected 60 kDa chymotrypsin fragment.

FIG. 5 illustrates the specific localization of the K16 crosslinking site within the GPIIb heavy chain according to Example ID. GPIIb:K16 complex was isolated as in FIG. 3 from reducing SDS-PAGE gels, and subjected to digestion with CNBr, chymotrypsin or SV8 protease. Thereafter the samples were analysed on SDS-PAGE and autoradiograms were produced to show the radioactive fragments. Intact (undigested) complex was analysed as a control. Thereafter the radioactive band from each digest was extracted and subjected to NH$_2$-terminal sequencing as in FIG. 4, and the resulting sequence is indicated in the figure for each digest. Amino acid residue positions within the GPIIb sequence are also indicated above each fragment sequence and correspond to the positions in FIG. 1.

FIG. 6 illustrates a diagrammatic representation of the analyses described in Figures 3-5 to establish the location of the K16 crosslinking site within GPIIb. The GPIIb light chain, consisting of 137 amino acids, and the heavy chain of 871 amino acids are drawn to scale in step 1. The results shown in FIG. 3 indicate that the light chain does not become crosslinked to the K16 peptide (Step 1). Immunoblotting with a GPIIb specific antibody PMI-1 in partial chymotryptic digests located the K16 crosslinking site to the amino terminal half of GPIIb heavy chain (Step 2). The 40 kDa fragment derived from CNBr digestion of GPIIb:K16 was determined to begin at the $NH_2$-terminus of GPIIb and is predicted to terminate at the methionine residue 314 (Step 3). Chymotryptic digest of GPIIb:K16 yielded a 7 kDa fragment beginning at residue 294 (Step 4). The 9 kDa SV8 derived fragment of GPIIb:K16 was determined to begin at residue 254, (Step 5). Therefore, the K16 crosslinking site consists of a 21 amino acid stretch on GPIIb heavy chain from residues 294–314. This region is boxed and indicated by the arrow in step 1.

DETAILED DESCRIPTION OF THE INVENTION

A. Definitions

Figure 4:
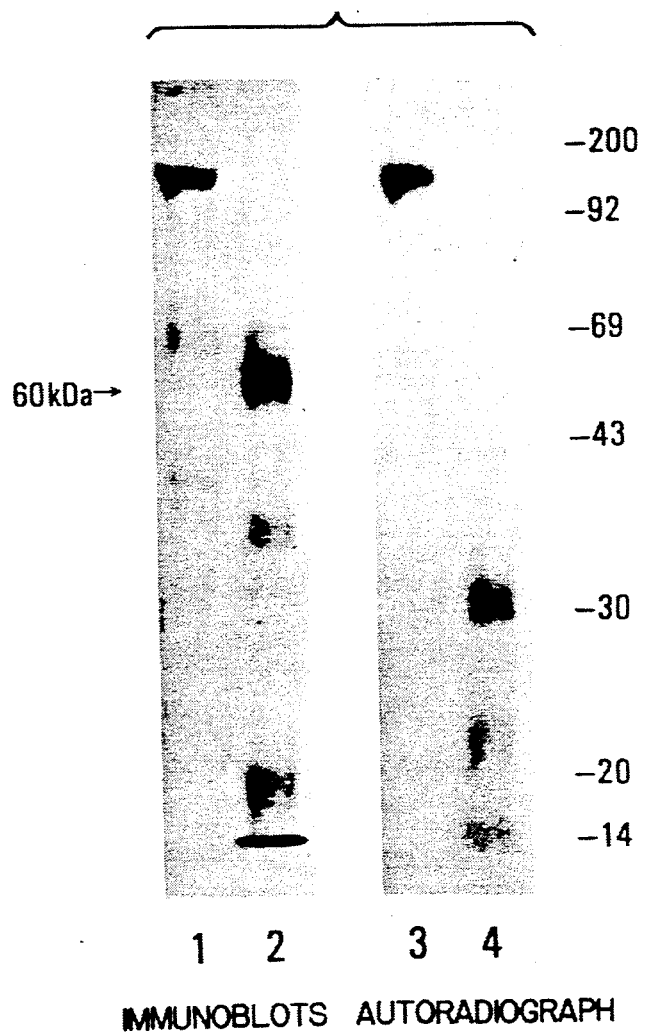

Amino Acid Residue: The amino acid residues described herein are preferred to be in the "L" isomeric form. However, residues in the "D" isomeric form can be substituted for any L-amino acid residue, as long as the desired functional property is retained by the polypeptide. NHz refers to the free amino group present at the amino terminus of a polypeptide. COOH refers to the free carboxyl group present at the carboxy terminus of the polypeptide. In keeping with standard polypeptide nomenclature, *J Biol. Chem.*, 243:3557-59, (1969), abbreviations for amino acid residues are as shown in the following Table of Correspondence:

| TABLE OF CORRESPONDENCE SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |

| -continued TABLE OF CORRESPONDENCE SYMBOL | | |
|---|---|---|
| 1-Letter | 3-Letter | AMINO ACID |
| D | Asp | aspartic acid |
| N | Asn | asparagine |
| C | Cys | cysteine |

It should be noted that all amino acid residue sequences are represented herein by formulae whose left to right orientation is in the conventional direction of amino-terminus to carboxyterminus. Furthermore, it should be noted that a dash at the beginning or end of an amino acid residue sequence indicates a peptide bond to a further sequence of one or more amino acid residues, or to an amino-terminal NHz group or to a carboxy-terminal COOH group.

Polypeptide and Peptide: Polypeptide and peptide are terms used interchangeably herein to designate a linear series of no more than about 100 amino acid residues connected one to the other by peptide bonds between the alpha-amino and carboxy groups of adjacent residues.

Nucleoside and Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide.

Base Pair (bp): A hydrogen-bonded partnership of adenine (A) with thymine (T), or of cytosine (C) with guanine (G) in a double stranded DNA molecule.

Receptor: Receptor and receptor protein are terms used herein to indicate a biologically active proteinaceous molecule that specifically binds to (or with) other molecules, referred to as ligands, to form a receptor-ligand protein complex.

Ligand: Ligand refers to a molecule that contains a structural portion that is bound by specific interaction with a particular receptor protein. A representative ligand and receptor are fibrinogen and the platelet glycoprotein GPIIb-IIIa.

B. Polypeptides

A polypeptide of the present invention has at least about 10, and no more than about 100, preferably no more than about 40, and more preferably no more than about 25 to 30, amino acid residues. In addition, a subject polypeptide is characterized as having an amino acid residue sequence homologous to, i.e., derived from the similar functional region of, that portion of the fibrinogen-binding region of GPIIb between residues 290-320 as shown in FIGS. 1-1 through 1-9.

By homologous to the fibrinogen-binding region of GPIIb is meant, as used herein, to define polypeptides having sequences derived from the ligand-binding region of an Integrin alpha subunit identified in Table 1, such as the region between residues 290 to 320 on GPIIb, or the homologous sequence found on the ligand-binding region of the alpha subunit of an Integrin including vitronection receptor (VnR), VLA-2, VLA-4, VLA-5, LFA-1 and Mac-1. As shown in Table 1, amino acid sequences from the identified ligand-binding region of an Integrin alpha subunit all have greater than 45% sequence similarity (homology) with the homologous GPIIb sequence.

In one embodiment, a subject polypeptide has a sequence that corresponds to the sequence of GPIIb shown in FIGS. 1-1 through 1-9 that includes an amino acid residue sequence represented by the formula: —TDVNGDGRHDL—, said polypeptide being capable of inhibiting the interaction between GPIIb and its native ligand, such as fibrinogen.

A native ligand as used in the context of an Integrin refers to the natural protein to which the Integrin binds in normal cellular interactive processes, ie., the respective ligand. In the case of GPIIb-IIIa, for example, a native ligand is fibrinogen; for the vitronectin receptor the native ligand is vitronectin; and for the fibronectin receptor the native ligand is fibronectin.

In another embodiment, a subject polypeptide has a sequence that corresponds to the sequence of VnR that includes an amino acid residue sequence represented by the formula: —TDINGDDYADV—, said polypeptide being capable of inhibiting the interaction between VnR and its native ligand, and to inhibit the adhesion of cells that contain VnR on their cell surface. The entire sequence of the alpha subunit of VnR is described in the article cited in the footnote to Table 1.

sented by the formula: —TDVNGDGLDDL—, said polypeptide being capable of inhibiting the interaction between VLA-5 and its native ligand, and to inhibit the adhesion of cells that contain VLA-5 on their cell surface. The entire sequence of the alpha subunit of VLA-5 is described in the article cited in the footnote to Table 1.

In another embodiment, a subject polypeptide has a sequence that corresponds to the sequence of LFA-1 that includes an amino acid residue sequence represented by the formula: —VDVDGDGETEL—, said polypeptide being capable of inhibiting the interaction between LFA-1 and its native ligand, and to inhibit the adhesion of cells that contain LFA-1 on their cell surface. The entire sequence of the alpha subunit of LFA-1 is described in the article cited in the footnote to Table 1.

In another embodiment, a subject polypeptide has a sequence that corresponds to the sequence of Mac-1 that includes an amino acid residue sequence represented by the formula: —VDVDSNGSTDL—, said polypeptide being capable of inhibiting the interaction between Mac-1 and its native ligand, and to inhibit the adhesion of cells that contain Mac-1 on their cell surface. The entire sequence of the alpha subunit of Mac-1

TABLE 1

Ligand-Binding Region[1] of GPIIb and other Alpha Subunits of the Integrin Family

| Integrin | Amino Acid Residue Sequence of the Ligand-Binding Region | % Identity to K16 Crosslinking Region | % Identity to overall GPIIb Sequence |
|---|---|---|---|
| GPIIb | AVTDVNGDGRHDL—LVGAPLYM | | |
| VnR | AATDINGDDYADV—FIGAPLFM | (57%) | 36% |
| VLA-2 | CSVDVDKDTITDVLLVGAPMYM | (52%) | 22% |
| VLA-4 | CAVDLNADGFSD—LLVGAPMQS | (48%) | 24% |
| VLA-5 | AATDVNGDGLDDL—LVGAPLLM | (81%) | 38% |
| LFA-1 | CGVDVDGDGETELLLIGAPLFY | (48%) | 30% |
| Mac-1 | CSVDVDSNGSTDLVLIGAPHYY | (48%) | 25% |
| P150,95 | CSVDVDTDGSTDLVLIGAPHYY | (52%) | 25% |

[1]The amino acid residue sequence of the ligand-binding region from GPIIb was determined in Example 1D by crosslinking to polypeptide K16 to be the ligand-binding region for binding to fibrinogen and corresponds to the residues 294-314 of GPIIb shown in FIGS. 1-1 through 1-9. The sequences shown for the other Integrin alpha subunits were obtained from the following citations, with the corresponding Integrin listed in parenthesis after the citation: Suzuki et al., J. Biol. Chem., 262:14080-85, 1987 (VnR); Takada et al., J. Cell Biol., 109:397-407, 1989 (VLA-2); Takada et al., EMBO J., 8:1361-68, 1989 (VLA-4); Argraves et al., J. Cell Biol., 105:1183-90, 1987 (VLA-5); Larson et al., J. Cell Biol., 108:703-12, 1989 (LFA-1); Corbi et al., J. Biol. Chem., 263:12403-11, 1988 (Mac-1); and Corbi et al., EMBO J., 6:4023-28, 1987 (p150,95); which references are hereby incorporated by reference.

In another embodiment, a subject polypeptide has a sequence that corresponds to the sequence of VLA-2 that includes an amino acid residue sequence represented by the formula: —VDVDKDTITDV—, said polypeptide being capable of inhibiting the interaction between VLA-2 and its native ligand, and to inhibit the adhesion of cells that contain VLA-2 on their cell surface. The entire sequence of the alpha subunit of VLA-2 is described in the article cited in the footnote to Table 1.

In another embodiment, a subject polypeptide has a sequence that corresponds to the sequence of VLA-4 that includes an amino acid residue sequence represented by the formula: —VDLNADGFSDL—, said polypeptide being capable of inhibiting the interaction between VLA-4 and its native ligand, and to inhibit the adhesion of cells that contain VLA-4 on their cell surface. The entire sequence of the alpha subunit of VLA-4 is described in the article cited in the footnote to Table 1.

In another embodiment, a subject polypeptide has a sequence that corresponds to the sequence of VLA-5 that includes an amino acid residue sequence repreis described in the article cited in the footnote to Table 1.

In another embodiment, a subject polypeptide has a sequence that corresponds to the sequence of P150,95 that includes an amino acid residue sequence represented by the formula: —VDVDTDGSTDL—, said polypeptide being capable of inhibiting the interaction between P150,95 and its native ligand, and to inhibit the adhesion of cells that contain P150,95 on their cell surface. The entire sequence of the alpha subunit of P150,95 is described in the article cited in the footnote to Table 1.

A preferred embodiment that is exemplary of the above embodiments for polypeptides that correspond to their respective Integrins is a polypeptide having an amino acid residue sequence that corresponds, and is preferably identical to, a formula shown in Table 2.

TABLE 2

| Formula Designation | Amino Acid Residue Sequence[1] |
|---|---|
| p1 | TDVNGDGRHDL |
| p2 | AVTDVNGDGRHDLLVGAPLYM |

TABLE 2-continued

| Formula Designation | Amino Acid Residue Sequence[1] |
| --- | --- |
| p3 | AATDINGDDYADUFIGAPLFM |
| p4 | CSVDVDKDTITDVLLVGAPMYM |
| p5 | CAVDLNADGFSDLLVGAPMQS |
| p6 | AATDVNGDGLDDLLVGAPLLM |
| p7 | CGVDVDGDGETELLLIGAPLFY |
| p8 | CSVDVDSNGSTDLVLIGAPHYY |
| p9 | CSVDVDTDGSTDLVLIGAPHYY |

[1]p1 and p2 have sequences that exactly correspond to the amino acid residue sequences shown in FIGS. 1-1 through 1-9 for GPIIb from residue 296 to 306, and from residue 294 to 314, respectively. p3 through p9 have sequences that exactly correspond to the amino acid residue sequences shown in Table 1 for the ligand-binding region of the alpha subunit of the Integrins, VnR, VLA-2, VLA-4, VLA-5, LFA-1, Mac-1 and In preferred embodiments a subject polypeptide is further characterized by its ability to competitively inhibit Integrin-mediated cell adhesion such as the aggregation of platelets, the adhesion of fibroblasts to a matrix, and the like. That is, a preferred subject polypeptide is able to competitively inhibit Integrin binding to a native ligand, i.e., a ligand to which the Integrin from which the polypeptide was derived binds in vivo.

Where the subject polypeptide contains an amino acid residue sequence from the fibrinogen binding region of GPIIb between residues 290 and 320, the polypeptide has the capacity to inhibit platelet adhesion, i.e., to act as an anti-thrombotic agent. Particularly preferred platelet adhesion-inhibiting polypeptides are the above-described polypeptides p1 and p2 whose adhesion-inhibiting properties are shown in Example 3.

In preferred embodiments a subject polypeptide is also further characterized by its ability, when used in an inoculum, to induce the production of a polyclonal antibody or monoclonal antibody of the present invention.

Amino acid residues present in a subject polypeptide in addition to a sequence corresponding to an above-described formula, can be any residues that do not materially affect the basic and novel characteristics of a polypeptide as are discussed herein. Such additional residues are usually added to one or both termini of an enumerated peptide and can include repeats and partial repeats of an enumerated peptide sequence or contiguous residues of the Integrin alpha subunit protein sequence.

A subject polypeptide has an amino acid residue sequence that corresponds to a portion of the ligand-binding region of an Integrin alpha subunit sequence. Thus, a polypeptide of the present invention need not be identical to the amino acid residue sequence of the ligand-binding portion of an Integrin alpha subunit, so long as it is able to exhibit at least one of the above preferred characteristics of a subject polypeptide. Therefore, a subject polypeptide can be subject to various changes, such as insertions, deletions and substitutions, either conservative or nonconservative, where such changes provide for certain advantages in their use.

Conservative substitutions are those where one amino acid residue is replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. The term "conservative substitution" also includes the use of a substituted amino acid in place of an unsubstituted parent amino acid provided that such a polypeptide also displays the requisite binding or inoculum activity.

When a polypeptide of the present invention has a sequence that is not identical to the sequence of an Integrin alpha subunit because one or more conservative or non-conservative substitutions have been made, usually no more than about 20% and more usually no more than 10% of the amino acid residues are substituted. An exception is where additional residues have been added at either terminus for the purpose of providing a "linker" by which the polypeptides of this invention can be conveniently affixed to a label or solid matrix, or antigenic carrier. Labels, solid matrices and carriers that can be used with the polypeptides of this invention are described hereinafter.

Amino acid residue linkers are usually at least one residue and can be 40 or more residues, more often 1 to 10 residues. Typical amino acid residues used for linking are tyrosine, cysteine, lysine, glutamic and aspartic acid, or the like. A representative linker is a Cys—Gly—Gly (CGG—) tripeptide attached to the amino terminus of a subject polypeptide by the carboxy terminal glycine residue of the linker, as is shown in Example 2. In addition, a polypeptide sequence of this invention can differ from the natural sequence by the sequence being modified by terminal-NH2 acylation, e.g., acetylation, or thioglycolic acid amidation, terminal-carboxlyamidation, e.g., ammonia, methylamine, etc.

When coupled to a carrier via a linker to form what is known in the art as a carrier-hapten conjugate, a subject polypeptide is capable of inducing antibodies that immunoreact with the Integrin alpha subunit to which the amino acid residue sequence of the polypeptide corresponds. In view of the well established principle of immunologic cross-reactivity, the present invention therefore contemplates antigenically related variants of a polypeptide having an amino acid residue sequence corresponding to a polypeptide having a formula shown in Table 2. An "antigenically related variant" is a polypeptide that immunoreacts with an antibody induced by a polypeptide according to formula shown in Table 2.

A subject polypeptide can be synthesized by any techniques that are known to those skilled in the polypeptide art. An excellent summary of the many techniques available may be found in J.M. Steward and J.D. Young, "Solid Phase Peptide Synthesis", W.H. Freeman Co., San Francisco, 1969, and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis.

A related embodiment contemplates a composition for promoting the attachment (adhesion) of cells to a substrate. Based on the ability of a subject polypeptide to compete with an Integrin for binding to the native ligand of the Integrin, the subject polypeptide provides a medium for ligand binding, and therefor can be used to promote cell attachment activity when the polypeptide is immobilized onto a substrate.

A composition containing a subject polypeptide is used to treat a substrate and thereby to immobilize the polypeptide contained in the composition onto the substrate.

The substrate can be any surface on which cell adhesion promoting activity is desired and includes containers for cell culture, medical devices, a prosthetic device, a synthetic resin fiber, a blood vessel or vascular graft, a percutaneous device, artificial organs and the like. The surface can be comprised of glass, a synthetic resin, nitrocellulose, polyester, agarose, collagen or a long chain polysaccharide.

Immobilization of polypeptides onto substrate, can be accomplished by a variety of means and depends, inter alia, on the substrate and the mechanism of immobilization desired. Methods for polypeptide immobilization or coupling are well known in the art and typically involve covalent linkages between a thiol or amino group on the polypeptide to a reactive group present on the substrate.

For example, of polypeptide immobilization methods see Aurameas et al., Scand J. Immunol., Vol. 8 Suppl. 7:7-23 (1978); U.S. Pat. Nos. 4,493,795, 4,578,079 and 4,671,950; Klipstein et al., J. Infect. Dis., 147:318-326 (1983) and Liu et al., Biochem., 80:690 (1979). For examples of the use of cell adhesion promoting polypeptides see U.S. Pat. No. 4,578,079.

C. Inocula

In another embodiment, a polypeptide of this invention, preferably a peptide corresponding to a formula shown in Table 2 or an antigenically related variant thereof is used in a pharmaceutically acceptable aqueous diluent composition to form an inoculum that, when administered in an effective amount, is capable of inducing antibodies that immunoreact with an Integrin alpha subunit to which the amino acid residue sequence of the polypeptide corresponds. The antibodies so induced are capable of inhibiting the Integrin-ligand interaction.

The word "inoculum" in its various grammatical forms is used herein to describe a composition containing a polypeptide of this invention as an active ingredient used for the preparation of antibodies against an Integrin alpha subunit.

When a polypeptide is used to induce antibodies it is to be understood that the polypeptide can be used alone, or linked to a carrier as a conjugate, or as a polypeptide polymer, but for ease of expression the various embodiments of the polypeptides of this invention are collectively referred to herein by the term "polypeptide", and its various grammatical forms.

As already noted, one or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, di-aldehydes such as glutaraldehyde, Klipstein et al., J. Infect. Dis., 147, 318-326 (1983) and the like, or the use of carbodiimide technology as in the use of a water-soluble carbodiimide to form amide links to the carrier. For a review of protein conjugation or coupling through activated functional groups, see Aurameas, et al., Scand. J. Immunol., Vol. 8, Suppl. 7:7-23 (1978).

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide or protein per unit dose depends, among other things, on the species of animal inoculated, the body weight of the animal and the chosen inoculation regimen as is well known in the art. Inocula typically contain polypeptide or protein concentrations of about 10 micrograms to about 500 milligrams per inoculation (dose), preferably about 50 micrograms to about 50 milligrams per dose.

The term "unit dose" as it pertains to the inocula of the present invention refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent or vehicle such as water, saline or phosphate-buffered saline to form an aqueous composition. Such diluents are well known in the art and are discussed, for example, in Remington's Pharmaceutical Sciences, 16th Ed., Mack Publishing Company, Easton, Pa. (1980) at pages 1465-1467.

Inocula can also include an adjuvant as part of the diluent. Adjuvants such as complete Freund's adjuvant (CFA), incomplete Freund's adjuvant (IFA) and alum are materials well known in the art, and are available commercially from several sources.

D. Polyclonal and Monoclonal Anti-peptide Antibodies

An antibody of the present invention immunoreacts with an Integrin alpha subunit epitope present in an epitope domain defined by an amino acid residue sequence corresponding to that of a subject polypeptide. In preferred embodiments, the epitope recognized by the antibody is one which can be formed (immunologically mimicked) by a subject polypeptide as evidenced by the ability of the polypeptide to competitively inhibit the binding of the antibody to the alpha subunit.

The ability of a subject antibody to recognize a portion of an epitope domain defined by an amino acid residue sequence corresponding to that of a subject polypeptide can be determined by methods well known in the art.

The term "antibody" in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v).

An "antibody combining site" is that structural portion of an antibody molecule comprised of a heavy and light chain variable and hypervariable regions that specifically binds (immunoreacts with) antigen. The term "immunoreact" in its various forms means binding between an antigenic determinant-containing molecule and a molecule containing an antibody combining site such as a whole antibody molecule or a portion thereof.

"Antigenic determinant" refers to the actual structural portion of the antigen that is immunologically bound by an antibody combining site. The term is also used interchangeably with "epitope".

1. Polyclonal Antibodies

A subject polyclonal antibody is further characterized as not immunoreacting with any Integrin beta subunit or an antigenic polypeptide having an amino acid residue sequence identical to sequences in the carboxy-terminal half of the Integrin alpha subunit to which the amino acid residue sequence of the subject polypeptide corresponds. Thus, for example, a subject polyclonal antibody does not immunoreact with a polypeptide whose sequence is shown in Table 3.

TABLE 3

| Polypeptides Derived from the Carboxy-Terminal Half of an Integrin Alpha Subunit | | |
|---|---|---|
| Integrin | Amino Acid Sequence Location | Amino Acid Residue Sequence |
| GPIIb | 784-799 | YELHNNGPGTVNGLHL |
| VnR | 810-825 | YELRNNGPSSFSKAML |
| VLA-2 | 946-960 | LKVTTGSVPVSMATV |
| VLA-4 | 775-791 | TFHVINTGNSMAPNVSV |
| VLA-5 | 830-845 | YELINQGPSSISQGVL |
| LFA-1 | 928-943 | YQVRIQPSIHDHVIPT |
| MaC-1 | 940-954 | YQVSNLGQRSLPISL |
| P150,95 | 936-950 | YQVNNLGQRDLPVSI |

[1]The amino acid residue sequences and the residue position numbers of the residues contained in the listed polypeptides are taken from the references cited in the footnote to Table 1.

A preferred polyclonal antibody of the present invention immunoreacts with a subject polypeptide, preferably a polypepetide corresponding in amino acid residue sequence to a formula shown in Table 2.

A preferred polyclonal antibody is characterized as having the ability to immunoreact with an Integrin alpha subunit and thereby inhibit the capacity of the Integrin to specifically bind to its ligand by an interaction with an ligand-containing protein. Thus, a subject polyclonal antibody is useful to inhibit, and thereby modulate, either in vivo or in vitro, the adhesion of cells that contain the Integrin with which the antibody immunoreacts.

In one embodiment, a preferred polyclonal antibody is characterized as having the ability to immunoreact with GPIIb and to inhibit the capacity of GPIIb to specifically bind fibrinogen.

Thus a preferred polyclonal antibody that immunoreacts with a subject polypeptide whose sequence is derived from the fibrinogen-binding region of GPIIb has the capacity to inhibit fibrinogen-GPIIb-IIIa ligand-receptor complex-mediated events, such as platelet adhesion, platelet aggregation and thrombus formation.

A polyclonal antibody of the present invention is typically produced by immunizing a mammal with an inoculum of the present invention, preferably an inoculum containing a peptide corresponding to a formula shown in Table 2, and thereby induce in the mammal antibody molecules having the appropriate polypeptide immunospecificity. The antibody molecules are then collected from the mammal and isolated to the extent desired by well known techniques such as, for example, by immunoaffinity chromatography using the immunizing polypeptide in the solid phase. The polyclonal antibody so produced can be used in, inter alia, the diagnostic methods and systems of the present invention to discriminate between activated and nonactivated platelets or nucleated cells and in therapeutic methods for the purpose of modulating cell adhesion, such as inhibiting platelet adhesion.

2. Monoclonal Antibodies

A monoclonal antibody of the present invention is characterized as immunoreacting with an epitope formed by the ligand-binding region of an Integrin alpha subunit that is homologous to residues 290-320 of GPIIb. Preferably, a subject monoclonal antibody is further characterized as immunoreacting with a subject polypeptide, preferably a polypeptide corresponding to a formula shown in Table 2.

A preferred monoclonal antibody is also characterized as having the ability to inhibit the specific binding of an Integrin to its ligand, such as is described above for polyclonal antibodies. A preferred monoclonal antibody that immunoreacts with a subject polypeptide derived from the fibrinogen-binding region of GPIIb, such as polypeptides p1 or p2, is further characterized as having the ability to inhibit the capacity of GPIIb to specifically bind fibrinogen, and to inhibit platelet adhesion.

Thus, in one embodiment, a monoclonal antibody is contemplated as comprising antibody molecules that immunoreact with a) GPIIb, and b) a polypeptide corresponding to the formula:
AVTDVNGDGRHDLLVGAPLYM A related embodiment contemplates a monoclonal antibody comprising monoclonal antibody molecules that immunoreact with a) a polypeptide having a sequence that corresponds to the formula:
TDVNGDGRHDL,
AVTDVNGDGRHDLLVGAPLYM,
AATDINGDDYADVFIGAPLFM,
CSVDVDKDTITDVLLVGAPMYM,
CAVDLNADGFSDLLVGAPMQS,
AATDVNGDGLDDLLVGAPLLM,
CGVDVDGDGETELLLIGAPLFY,
CSVDVDSNGSTDLVLIGAPHYY, or
CSVDVDTDGSTDLVLIGAPHYY;
and b) the alpha subunit of an Integrin to which the amino acid residue sequence of said polypeptide corresponds.

The phrase "monoclonal antibody" in its various grammatical forms refers to a population of antibody molecules that contain only one species of antibody combining site capable of immunoreacting with a particular antigen. A monoclonal antibody composition thus typically displays a single binding affinity for any antigen with which it immunoreacts. A monoclonal antibody composition may therefore contain an antibody molecule having a plurality of antibody combining sites, each immunospecific for a different antigen, e.g., a bispecific monoclonal antibody.

A monoclonal antibody is typically composed of antibodies produced by clones of a single cell called a hybridoma that secretes (produces) but one kind of antibody molecule. The hybridoma cell is formed by fusing an antibody-producing cell and a myeloma or other self-perpetuating cell line. Such antibodies were first described by Kohler and Milstein, *Nature* 256:495-497 (1975), which description is incorporated by reference.

3. Methods for Producing A Monoclonal Antibody

The present invention contemplates a method of forming a monoclonal antibody that (a) immunoreacts with (a) a subject polypeptide, and (b) the Integrin alpha subunit to which the amino acid residue sequence corresponds. The method comprises the steps of:

(a) Immunizing an animal with an integrin alpha subunit or a subject polypeptide. This is typically accomplished by administering an immunologically effective amount i.e., an amount sufficient to produce an immune response, of the immunogen to an immunologically competent mammal. Preferably, the mammal is a rodent such as a rabbit, rat or mouse. The mammal is then maintained for a time period sufficient for the mammal to produce cells secreting antibody molecules that immunoreact with the immunogen.

(b) A suspension of antibody-producing cells removed from the immunized mammal is then prepared. This is typically accomplished by removing the spleen of the mammal and mechanically separating the individual spleen cells in a physiologically tolerable medium using methods well known in the art.

(c) The suspended antibody-producing cells are treated with a transforming agent capable of producing a transformed ("immortalized") cell line. Transforming agents and their use to produce immortalized cell lines are well known in the art and include DNA viruses such as Epstein Bar Virus (EBV), Simian Virus 40 (SV40), Polyoma Virus and the like, RNA viruses such as Moloney Murine Leukemia Virus (Mo-MuLV), Rous Sarcoma Virus and the like, myeloma cells such as P3X63-Ag8.653, Sp2/0-Ag14 and the like.

In preferred embodiments, treatment with the transforming agent results in the production of a hybridoma by fusing the suspended spleen cells with mouse myeloma cells from a suitable cell line by the use of a suitable fusion promoter. The preferred ratio is about 5 spleen cells per myeloma cell in a suspension containing about $10^8$ splenocytes.

The cell line used should preferably be of the so-called "drug resistant" type, so that unused myeloma cells will not survive in a selective medium, while hybrids will survive. The most common class is 8-azaguanine resistant cell lines, which lack the enzyme hypoxanthine guanine phophoribosyl transferase and hence will not be supported by HAT (hypoxanthine, aminopterin, and thymidine) medium. It is also generally preferred that the myeloma cell line used be of the so-called "non-secreting" type, in that it does not itself produce any antibody, although secreting types may be used. In certain cases, however, secreting myeloma lines may be preferred. While the preferred fusion promoter is polyethylene glycol having an average molecule weight from about 1000 to about 4000 (commercially available as PEG 1000, etc.), other fusion promoters known in the art may be employed.

(d) The transformed cells are then cloned, preferably to monoclonality. The cloning is preferably performed in a tissue culture medium that will not support non-transformed cells. When the transformed cells are hybridomas, this is typically performed by diluting and culturing in separate containers, the mixture of unused spleen cells, unused myeloma cells, and fused cells (hybridomas) in a selective medium which will not support the unused myeloma cells for a time sufficient to allow death of the unused cells (about one week). The dilution may be a type of limiting one, in which the volume of diluent is statistically calculated to isolate a certain number of cells (e.g., 1-4) in each separate container (e.g., each well of a microliter plate). The medium is one (e.g., HAT medium) which will not support the drug-resistant (e.g., 8-azaguanine resistant) unused myeloma cell line.

(e) The tissue culture medium of the cloned transformants is evaluated for the presence of secreted antibody molecules that immunoreact with the immunogen and its corresponding subject polypeptide or Integrin alpha subunit.

(f) Once a desired transformant has been identified in step (e), it is selected and grown in a suitable tissue culture medium for a suitable length of time, followed by recovery of the desired antibody from the culture supernatant. The suitable medium and suitable length of culturing time are known or are readily determined.

To produce a much greater concentration of slightly less pure monoclonal antibody, the desired hybridoma may be injected into mice, preferably syngeneic or semisyngeneic mice. The hybridoma will cause formation of antibody-producing tumors after a suitable incubation time, which will result in a high concentration of the desired antibody (about 5-20 mg/ml) in the bloodstream and peritoneal exudate (ascites) of the host mouse.

Media useful for the preparation of these compositions are both well known in the art and commercially available and include synthetic culture media, inbred mice and the like. An exemplary synthetic medium is Dulbecco's minimal essential medium [DMEM; Dulbecco et al., *Virol.* 8:396 (1959)] supplemented with 4.5 gm/1 glucose, 20 mm glutamine, and 20% fetal calf serum. An exemplary inbred mouse strain is the Balb/c.

A monoclonal antibody of the present invention can also be further purified by well known immunoaffinity chromatography methods by using in the solid phase a subject polypeptide with which the antibody immunoreacts.

A monoclonal antibody produced by the above method can be used, for example, in diagnostic and therapeutic modalities wherein formation of an Integrin alpha subunit immunoreaction product is desired. Exemplary reaction products include a GPIIb-containing immunoreaction product.

E. Hybridomas and Methods of Preparation

Hybridomas of the present invention are those characterized as having the capacity to produce a subject monoclonal antibody.

A preferred hybridoma of the present invention is characterized as producing antibody molecules that also immunoreact with a cytoadhesin, preferably GPIIb.

Methods for producing hybridomas that produce, e.g., secrete, antibody molecules having a desired immunospecificity, i.e., having the ability to immunoreact with a particular protein, an identifiable epitope on a particular protein, and/or a polypeptide, are well known in the art. Particularly applicable is the hybridoma technology described by Niman et al., *Proc. Natl. Acad. Sci. USA*, 80:4949-4953 (1983), and by Galfre et al., *Meth. Enzymol.*, 73:3-46 (1981), which descriptions are incorporated herein by reference. An exemplary method was described in the above disclosure for producing a monoclonal antibody.

F. Therapeutic Methods and Compositions

A subject polypeptide can be used to modulate the adhesion in vivo of cells expressing the Integrin alpha subunit to which the polypeptide corresponds.

For instance, a subject polypeptide corresponding to formula p1 or p2, or both, can be used in a pharmaceutically acceptable composition that, when administered to a human subject in an effective amount, is capable of competitively inhibiting the aggregation of platelets. That inhibition is believed to result in a decreased rate of thrombus formation. Thus, in vivo administration of a subject polypeptide can be used to modulate any physiological response initiated by adhesion such as coagulation and some inflammatory responses.

In another embodiment, the normal cellular adhesion functions of a cell bearing an Integrin on its surface can be inhibited or modulated by intravenous administration of an effective amount of a pharmaceutically acceptable composition comprising a polyclonal or monoclonal antibody of this invention that immunoreacts with the alpha subunit of the Integrin on the surface of the cell to be inhibited.

In a preferred embodiment, the aggregation of platelets can be inhibited by intravenous administration of an effective amount of a pharmaceutically acceptable composition comprising a subject polyclonal antibody that immunoreacts with a polypeptide corresponding to a portion of the fibrinogen-binding region of GPIIb, such as a polypeptide according to formula p1 or p2.

A preferred method of modulating platelet adhesion contemplates administering a platelet aggregation-inhibiting amount of a subject monoclonal antibody that immunoreacts with the fibrinogen-binding region (residues 290–320) of GPIIb. More preferably, the monoclonal antibody used in a platelet aggregation-inhibiting therapeutic method is further characterized as immunoreacting with a polypeptide corresponding to formula p1 or p2.

Insofar as polyclonal or monoclonal antibodies can be used therapeutically to modulate cell adhesion-mediated events, the present invention also contemplates the use of a subject polypeptide to neutralize the modulating effect of therapeutically administered antibodies, e.g., as an antidote for the anti-polypeptide antibody.

In one manner of practicing this embodiment, an anti-thrombotic antibody-containing therapeutic reagent is first administered to a patient to modulate cell adhesion, platelet aggregation or thrombus formation. Thereafter, upon the onset of a bleeding complication, or when it becomes desirable to neutralize the anti-thrombotic effects of the administered antibody, an amount of a subject polypeptide is administered that is effective to immunoreact with the administered antibody and thereby neutralize the modulating effect of the antibody.

The choice of polypeptide to be administered as an antidote depends upon the antibody to be neutralized, and requires that the administered polypeptide have the capacity to immunoreact with the administered antibody.

The polypeptide- or antibody molecule-containing compositions administered take the form of solutions or suspensions, however, polypeptides can also take the form of tablets, pills, capsules, sustained release formulations or powders. In any case, the polypeptide-containing compositions typically contain about 0.1 uM to about 1.0 M of polypeptide as active ingredient, preferably about 1.0 uM to about 10 millimolar (mM), whereas the antibody molecule-containing compositions typically contain about 10 ug/ml to about 20 mg/ml of antibody as active ingredient, preferably about 1 mg/ml to about 10 mg/ml.

The preparation of a therapeutic composition that contains polypeptides or antibody molecules as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient as are well known. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide or antibody can be formulated into the therapeutic composition as neutralized pharmaceutically acceptable salt forms. Pharmaceutically acceptable salts include the acid addition salts (formed with the free amino groups of the polypeptide or antibody molecule) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide- or antibody containing compositions are conventionally administered intravenously, as by injection of a unit dose, for example. The term "unit dose" when used in reference to a therapeutic composition of the present invention refers to physically discrete units suitable as unitary dosages for humans, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject to utilize the active ingredient, and degree of inhibition of receptor-ligand binding desired. Precise amounts of active ingredient required to be administered depend on the judgment of the practitioner and are peculiar to each individual. However, suitable dosage ranges are of the order of one to several milligrams of active ingredient per individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain therapeutically effective concentrations in the blood are contemplated. For a subject polypeptide, therapeutically effective blood concentrations are in the range of about 1.0 uM to about 10 mM, preferably about 50 uM to about 1.0 mM. Therapeutically effective blood concentrations of antibody molecules of the present invention are in the range of about 0.1 uM to about 10 uM, preferably 1.0 uM.

G. Diagnostic Systems

A diagnostic system in kit form of the present invention includes, in an amount sufficient for at least one assay, a polypeptide, polyclonal antibody or monoclonal antibody of the present invention as a separately packaged reagent. Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In one embodiment, a diagnostic system for assaying for activated platelets in a platelet-containing vascular fluid sample, such as blood or plasma, comprises a package containing a subject polyclonal antibody that immunoreacts with a polypeptide corresponding to formula p1 or p2. In another embodiment, a diagnostic system for assaying for activated platelets in a platelet-containing vascular fluid sample comprises a package containing a subject monoclonal antibody that immunoreacts with an epitope formed by the fibrinogen-binding region (residues 290-320) of GPIIb, and preferably also immunoreacts with a polypeptide corresponding to formula p1 or p2. A diagnostic system may also include a subject polypeptide where the assay method to be performed by the diagnostic system utilizes a competitive immunoreaction format. Further preferred are kits wherein the antibody molecules of the polyclonal or monoclonal antibody are linked to a label.

Thus, in preferred embodiments, a diagnostic system of the present invention further includes a label or indicating means capable of signaling the formation of a complex containing the antibody molecules of a polyclonal or monoclonal antibody of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. "In vivo" labels or indicating means are those useful within the body of a human subject and include $^{111}$In, $^{99}$Tc, $^{Ga}$, $^{186}$Re, and $^{132}$I. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel protein methods and/or systems.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas, et al., *Scand. J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention but is not itself a protein expression product, polypeptide, or antibody molecule of the present invention. Exemplary specific binding agents are antibody molecules, complement proteins or fragments thereof, protein A and the like. Preferably, the specific binding agent can bind the antibody molecule or polypeptide of this invention when it is present as part of a complex.

In preferred embodiments the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the presence or quantity of fibrinogen-bound platelets in a body fluid sample such as serum, plasma or urine. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of *Basic and Clinical Immunology* by D.P. Sites et al., published by Lange Medical Publications of Los Altos, Ca. in 1982 and in U.S. Pat. No. 3,654,090; U.S. Pat. No. 3,850,752; and U.S. Pat. No. 4,016,043, which are all incorporated herein by reference.

Thus, in preferred embodiments, the expressed protein, polypeptide, or antibody molecule of the present invention can be affixed to a solid matrix to form a solid support that is separately packaged in the subject diagnostic systems.

The reagent is typically affixed to the solid matrix by adsorption from an aqueous medium although other modes of affixation, well known to those skilled in the art can be used.

Useful solid matrices are well known in the art. Such materials include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microliter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microliter plate and one or more buffers can also be included as separately packaged elements in this diagnostic assay system.

The packages discussed herein in relation to diagnostic systems are those customarily utilized in diagnostic systems. Such packages include glass and plastic (e.g., polyethylene, polypropylene and polycarbonate) bottles, vials, plastic and plastic-foil laminated envelopes and the like.

H. Assay Methods

The present invention contemplates any method that results in detecting an Integrin alpha subunit, and particularly GPIIb, by producing a complex containing an antibody molecule contained in a polyclonal antibody or monoclonal antibody of the present invention. Those skilled in the art will understand that there are numerous well known clinical diagnostic chemistry procedures that can be utilized to form those complexes. Various heterogeneous and homogeneous assay protocols can be employed, either competitive or non-competitive for detecting the presence of an Integrin alpha subunit in a body sample. Thus, while exemplary assay methods are described herein, the invention is not so limited.

For example, a heparin-preserved (non-clotted) blood sample and $^{125}$I-labeled antibody molecules are admixed. The immunoreaction admixture thus formed is maintained under immunological assay conditions for a time period sufficient for any activated platelets to immunoreact with the labeled antibodies and form a labeled immunoreaction product. The labeled immunoreaction products are then separated from the non-reacted labeled-antibodies, typically by centrifugation sufficient to pellet all platelets present in the sample. The amount of labeled immunoreaction product formed is then assayed.

Immunological assay conditions are those that maintain the immunological activity of the antibody molecules contained in a polyclonal or monoclonal antibody of this invention and the Integrin molecules sought to be assayed. Those conditions include a temperature range of about 4 degrees C. to about 45 degrees C., preferably about 37 degrees C., a pH value range of about 5 to about 9, preferably about 7 and an ionic strength varying from that of distilled water to that of about one molar sodium chloride, preferably about that of physiological saline. Methods for optimizing such conditions are well known in the art.

I. DNA Segments

In living organisms, the amino acid residue sequence of a protein or polypeptide is directly related via the genetic code to the deoxyribonucleic acid (DNA) sequence of the structural gene that codes for the protein. Thus, a structural gene can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences can code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

A DNA segment of the present invention comprises no more than about 2000 nucleotide base pairs and includes a structural gene that encodes a subject polypeptide containing an Integrin alpha subunit amino acid residue sequence homologous to the GPIIb sequence located between amino acid residues 290-320 as shown in FIGS. 1-1 through 1-9.

A preferred DNA segment of the present invention includes a DNA sequence that codes for an amino acid residue sequence corresponding to, and preferably identical to, a sequence represented by a polypeptide having a formula as shown in Table 2. Preferably, the DNA sequence is present as an uninterrupted linear series of codons where each codon codes for an amino acid residue found in the above described amino acid residue sequences, i.e., the DNA sequence contains no introns.

Thus, a preferred DNA segment consisting essentially of the nucleotide sequence shown in FIGS. 1-1 through 1-9 from about base 980 to about base 1012 constitutes one embodiment of the present invention.

A DNA segment of the present invention can easily be synthesized by chemical techniques, for example, the phosphotriester method of Matteucci et al., *J. Am. Chem. Soc.*, 103:3185 (1981). Of course, by chemically synthesizing the coding sequence, any desired modifications can be made simply by substituting the appropriate bases for those encoding the native amino acid residue sequence. However, DNA molecules including sequences exactly homologous to those shown in FIGS. 1-1 through 1-9 are preferred.

The DNA molecules of the present invention typically have cohesive termini, i.e., "overhanging" single-stranded portions that extend beyond the double-stranded portion of the molecule. The presence of cohesive termini on the DNA molecules of the present invention is preferred.

Also contemplated by the present invention are ribonucleic acid (RNA) equivalents of the above described DNA segments.

J. Recombinant DNA Molecules

A recombinant DNA molecule of the present invention can be produced by operatively linking a vector to a DNA segment of the present invention, preferably a DNA segment coding for a subject polypeptide corresponding to a formula shown in Table 2.

As used herein, the term "vector" refers to a DNA molecule capable of autonomous replication in a cell and to which another DNA segment can be operatively linked so as to bring about replication of the attached segment. Vectors capable of directing the expression of genes encoding proteins having GPIIb-related amino acid residue sequences are referred to herein as "expression vectors". Thus, a recombinant DNA molecule (rDNA) is a hybrid DNA molecule comprising at least two nucleotide sequences not normally found together in nature.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of the gene encoding a polypeptide having an Integrin alpha subunit-related amino acid residue sequence included in DNA segments to which it is operatively linked.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the gene encoding a GPIIb-related amino acid residue sequence in a bacterial host cell, such as E. coli, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Bio-Rad Laboratories, (Richmond, Ca.) and pPL and pKK223 available from Pharmacia, Piscataway, N.J.

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), and pTDT1 (ATCC, #31255).

In preferred embodiments, the eucaryotic cell expression vectors used to construct the recombinant DNA molecules of the present invention include a selection marker that is effective in a eucaryotic cell, preferably a drug resistance selection marker. A preferred drug resistance marker is the gene whose expression results in neomycin resistance, i.e., the neomycin phosphotransferase (neo) gene. Southern et al., *J. Mol. Appl. Genet.*, 1:327-341 (1982).

The use of retroviral expression vectors to form the rDNAs of the present invention is also contemplated. As used herein, the term "retroviral expression vector" refers to a DNA molecule that includes a promoter sequence derived from the long terminal repeat (LTR) region of a retrovirus genome.

In preferred embodiments, the expression vector is typically a retroviral expression vector that is preferably replication-incompetent in eucaryotic cells. The construction and use of retroviral vectors has been described by Sorge et al., *Mol. Cell. Biol.*, 4:1730-37 (1984).

A variety of methods have been developed to operatively link DNA to vectors via complementary cohesive termini. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. A DNA segment having cohesive termini is treated with bacteriophage T4 DNA polymerase or E. coli DNA polymerase I, enzymes that remove protruding, 3', single-stranded termini with their 3'-5' exonucleolytic activities and fill in recessed 3' ends with their polymerizing activities. The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies, Inc., New Haven, Conn.

Also contemplated by the present invention are RNA equivalents of the above described recombinant DNA molecules.

K. Transformed Cells and Cultures

The present invention also relates to a host cell transformed with a recombinant DNA molecule of the present invention. The host cell can be either procaryotic or eucaryotic. Bacterial cells are preferred procaryotic host cells and typically are a strain of E. coli such as, for example the E. coli strain DH5 available from Bethesda Research Laboratories, Inc., Bethesda, Md. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61 and NIH Swiss mouse embryo cells NIH/3T3 available from the ATCC as CRL 1658.

Transformation of appropriate host cells with a recombinant DNA molecule of the present invention is accomplished by well known methods that typically depend on the type of vector used. With regard to transformation of procaryotic host cells, see, for example, Cohen et al., *Proc. Natl. Acad. Sci. USA*, 69:2110 (1972); and Maniatis et al., *Molecular Cloning, A Laboratory Mammal*, Cold Spring Harbor Laboratory, Cold Spring Harbor, N.Y. (1982). With regard to transformation of vertebrate cells with retroviral vectors containing rDNAs, see, for example, Sorge et al., *Mol. Cell. Biol.*, 4:1730-37 (1984); Graham et al., *Virol.*, 52:456 (1973); and Wigler et al., *Proc. Natl. Acad. Sci. USA*, 76:1373-76 (1979).

Successfully transformed cells, i.e., cells that contain a recombinant DNA molecule of the present invention, can be identified by well known techniques. For example, cells resulting from the introduction of an rDNA of the present invention can be cloned to produce monoclonal colonies. Cells from those colonies can be harvested, lysed and their DNA content examined for the presence of the rDNA using a method such as that described by Southern, *J. Mol. Biol.*, 98:503 (1975) or Berent et al., *Biotech.*, 3:208 (1985).

In addition to directly assaying for the presence of rDNA, successful transformation can be confirmed by well known immunological methods when the rDNA is capable of directing the expression of a subject polypeptide. For example, cells successfully transformed with a subject rDNA containing an expression vector produce a polypeptide displaying a characteristic antigenicity. Samples of a culture containing cells suspected of being transformed are harvested and assayed for a subject polypeptide using antibodies specific for that polypeptide antigen, such as those produced by a hybridoma of the present invention.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains a protein displaying Integrin beta subunit antigenicity.

Nutrient media useful for culturing transformed host cells are well known in the art and can be obtained from several commercial sources. In embodiments wherein the host cell is mammalian, a "serum-free" medium is preferably used.

L. Methods for Producing A Subject Polypeptide

Another aspect of the present invention pertains to a method for producing a subject polypeptide useful for raising antibodies which can be used in the diagnostic systems and methods of the present invention.

The present method entails initiating a culture comprising a nutrient medium containing host cells transformed with a recombinant DNA molecule of the present invention that is capable of expressing a gene encoding a subject polypeptide, preferably a polypeptide corresponding to a formula shown in Table 2. The culture is maintained for a time period sufficient for the transformed cells to express the subject polypeptide. The expressed polypeptide is then recovered from the culture.

Methods for recovering an expressed polypeptide from a culture are well known in the art and include fractionation of the polypeptide-containing portion of the culture using well known biochemical techniques. For instance, the methods of gel filtration, gel chromatography, ultrafiltration, electrophoresis, ion exchange, affinity chromatography and the like, such as are known for protein fractionations, can be used to isolate the expressed proteins found in the culture. In addition, immunochemical methods, such as immunoaffinity, immunoabsorption and the like can be performed using well known methods.

EXAMPLES

The following examples are intended to illustrate, but not limit, the present invention.

1. Identification of a Ligand Binding Region on an Integrin

Chemical crosslinking has been used extensively to study the interactions of RGD-containing ligands with GPIIb-IIIa. Bennett et al., *J. Biol. Chem.*, 257:8049 (1982). Most recently, crosslinking approaches have been used to examine the interaction of small RGD peptides of six to fourteen amino acids with GPIIb-IIIa as a means of characterizing the topography of the RGD recongnition site. Santero et al., *Cell*, 48:867 (1987) and D'Souza et al., *J. Biol. Chem.*, 263:3943 (1988). These studies have shown that platelet activation with agonist, an event necessary for binding of adhesive proteins such as fibrinogen and fibronectin to GPIIb-IIIa, markedly and selectively enhances the crosslinking of the RGD-peptides to GPIIIa, the beta subunit of the Integrin GPIIb-IIIa.

The present study defines a discrete site within GPIIb to which a small fibrinogen derived peptide can be chemically crosslinked. That site is believed to define a general functional site for ligand binding to the alpha subunit of Integrin, and is referred to herein as the ligand-binding region on the alpha subunit of Integrin. The amino acid residue sequence of this region is relatively conserved in members of the Integrin family (Table 1) indicating it plays a critical role in the function of this family of adhesion receptors.

A. Fibrinogen-Peptide Preparation

The peptide used in this study, designated K16 and derived from fibrinogen gamma chain, has the amino acid residue sequence KYGGHHLGGAKQAGDV. This peptide was designed to contain a lysine residue (K) to facilitate crosslinking and a tyrosine residue (Y) to provide a site for radioiodination. K16 was prepared by solid-phase synthesis on an Applied Biosystems model 430 peptide synthesizer (Foster City, Ca.) using peptidylglycine a-amidating monooxygenase resins and t-Boc amino acids purchased from Applied Biosystems. The peptide was analyzed for homogeneity by high performance liquid chromatography using a C18 μ Bondapak column with a linear gradient of 0–60% acetonitrile in 0.1% trifluoroacetic acid and was found to be >85% homogeneous. The amino acid composition of the peptide was determined after about a 24 hour period, the hydrolysates being in 6 N HCl, and the results were consistent with theoretical yields. Peptides were dissolved in phosphate buffered saline (PBS) prior to use and the pH was adjusted to 7.2. Other polypeptides described herein are also prepared by the above procedure.

K16 was radioiodinated by a modified lactoperoxidase-glucose oxidase method see Lam et al., *J. Biol. Chem.*, 262:947–950 (1987). Briefly, glucose (40 μg in 80 μl of 0.2 M sodium phosphate, pH 7.4), carrier-free $Na^{125}$ (15 milliCuries) and Enzymobead reagent (BioRad, Richmond, Ca.) were added to 10 mg of K16 peptide, and the reaction carried out according to the Enzymobead manufacturer's instructions. Thereafter, the iodonated peptide was separated from the other reagents by gel filtration on a Bio-Gel P-2 column. The conditions for radioiodination were selected to minimize ligand heterogeneity, and >80% of the iodinated peptide was in the monoiodotyrosinated form using this protocol. The concentration of the labeled peptide was determined by absorbance at 280 nm, using extinction coefficients derived from the amino acid compositions. The specific activity of the peptide was about 5–8 mCi/mg.

B. Platelet Preparation and Chemical Crosslinking of Peptide K16 to Discrete Sites on GPIIb Platelets were isolated from fresh human blood collected into acid/citrate/dextrose by differential centrifugation followed by gel filtration on Sepharose 2B in divalent ion-free Tyrode's buffer, pH 7.3, containing 0.1% bovine serum albumin. See, Marguerie et al., *J. Biol. Chem.*, 225:154–161 (1980).

Platelet binding of K16 followed the protocols previously described for measuring platelet interactions with adhesive proteins and with this and other peptides. See, Ginsberg et al., *J. Biol. Chem.*, 260:3931–3936 (1985); Lam et al., *Fed. Proc. Fed. Am. Soc. Exp. Biol.*, 44:1126

(1985); and Marguerie et al., supra. Briefly, platelets were suspended at $4 \times 10^8$/ml in divalent ion-free Tyrode's albumin buffer. Unless otherwise specified, $Ca^{2+}$ was added to a final concentration of 1 mM. The platelet stimulus used was 0.5 unit/ml alpha-thrombin. In assays in which fibrinogen and thrombin were present, 30 nM D-phenylalanyl-L-prolyl-arginine ketone (Calbiochem, La Jolla, Ca.) was added to the platelet suspension 5 minutes after addition of thrombin and 5 minutes before addition of fibrinogen. The radiolabeled peptide was then added to $6 \times 10^8$ cells/ml stimulated or nonstimulated platelets at a concentration of 30 μM, and binding proceeded for 45 min at 22° C. The selected cross-linking agent was then added. The cross-linking agent used in this study, bis(sulfosuccinimidyl) suberate ($BS^3$), purchased from Pierce Chemical Co. was dissolved in PBS immediately prior to use and admixed with the platelets to a final concentration of 0.2 mM. The cross-linking reactions were terminated after 10 min at 22° C. by addition of 10 mM Tris, pH 7.0.

The cell-bound ligand was recovered by centrifugation through 20% sucrose, and the cells were extracted in PBS containing 1% Nonidet P40 and 10 mM N-ethylmaleimide (Sigma). Extrated proteins were precipitated with 10% trichloroacetic acid, and the pellet obtained after centriguation was washed three times with cold 85% ethanol. The cross-linked samples were analyzed by electrophoresis (SDS-PAGE) on polyacrylamide vertical slab gels in the buffer system of Laemmli, *Nature*, 227 680-635 (1970). For disulfide bond reduction, the samples were treated with 5% 2-mercaptoethanol. Gels were dried and autoradiograms were developed with Kodak X-Omat AR films. Molecular weights were estimated on the basis of electrophoretic mobility relative to standards obtained from Diversified Biotech (MA).

C. Immunoblotting Procedures

Cross-linked samples were immunoprecipitated using a monoclonal antibody designated PMI-1, which recognizes the heavy chain of GPIIb. Loftus et al., *Proc. Natl. Acad. Sci. USA.* 84:7114 (1987). Washed acid-precipitates, obtained from the cross-linked samples as described above, were dissolved in 250 μl of immunoprecipitation buffer (IPB) which contained 0.15 M NaCl, 0.01 M EDTA, 10 mM benzamidine-HCl, soybean trypsin inhibitor (10 μg/ml), 0.2 mM phenylmethanesulfonyl fluoride, 1% (v/v) Triton X-100, 0.05% Tween 20, 0.02% $NaN_3$, and Trasylol (5 units/ml) in 0.02 M Tris-HCl, Ph 7.4. The IPB has been found to dissociate the complex of GPIIb-IIIa. The samples were precleared by adding 15 μl of heat-inactivated normal rabbit serum followed by protein A reagent (Pansorbin, Behring Diagnostics). The cleared lysates were then supplemented with 1% bovine serum albumin and 150 μl of IPB containing 10 μl of the above monoclonal antibody. Samples were incubated overnight at 4° C., and Pansorbin was then added. After 1 h at 22° C., samples were centrifuged, and the recovered immunoprecipitates were washed three times by centrifugation in IPB. The precipitates were solubilized by heat for 3 min at 100° C. in Laemmli sample buffer and then subjected to SDS-PAGE as described above. For immunoblotting, protein samples were resolved on SDS-PAGE as indicated above. After electrophoresis, the resolved proteins were transferred onto polyvinylidene difluoride membranes (PVDF). The transfers were probed with the anti-GPIIb monoclonal antibody, PMI-1, or with a rabbit antiserum raised to a peptide having a sequence corresponding to the heavy or light chains of GPIIb. Loftus et al., *J. Biol. Chem.*, 263:11025-28 (1988). The bound antibodies were detected using anti-mouse or anti-rabbit IgG conjugated to horseradish peroxidase (Bio-Rad) and 4-chloro-1-napthol as substrate.

FIG. 2A shows an autoradiogram of $^{125}$I-K16 cross-linked to thrombin-stimulated platelets according to the above procedures. The radioactivity migrated as a single, major band with an electrophoretic mobility identical to GPIIb. Minimal radioactivity was detected at the GPIIIa position. A 50-fold excess of nonlabeled K16 abolished the crosslinking of the radiolabeled peptide to the cells (FIG. 2A, right lane), providing an initial indication of specificity. That the major radioactive band was authentic GPIIb was demonstrated by its immunoprecipitation with a monoclonal antibody to GPIIb (FIG. 2B). Shadle et al., *J. Cell Biol;* 99 2056-60 (1984). This antibody, PMI-1, immunoprecipitated the major radioactive band within the platelet extract while numerous control antibodies, including a monoclonal of the same subclass to another platelet protein, failed to immunoprecipitate the radioactive band. During the course of numerous crosslinking experiments, variable amounts of radioactive material were found to accumulate on top of the gels. The immunoprecipitation experiment shown in FIG. 2B indicates that at least a portion of the high molecular weight radioactivity contained GPIIb antigen.

Platelet activation markedly affected the crosslinking of $^{125}$I-K16 to GPIIb (FIG. 2C). ADP, PMA and thrombin all increased the crosslinking of K16 to GPIIb relative to that observed with unstimulated platelets. The most pronounced enhancement of K16 crosslinking was observed with thrombin as the platelet stimulus. Relative to nonactivated platelets, thrombin stimulation increased the K16 crosslinking to GPIIb by 12-fold (4 experiments). The augmentation of crosslinking was due to an increase in K16 binding to the stimulated cells as well as to an increase in the efficiency of the crosslinking reaction. The enhanced crosslinking of the peptide to GPIIb on stimulated platelets was also observed with two additional crosslinking reagents, 3,3'-dithiobis (sulfosuccinimidyl propionate) and dithiobis (succinimidyl propionate).

With the above data providing clear evidence for specific crosslinking of the K16 peptide to a relevant site, localization of the site within the GPIIb subunit was determined by the following procedures. The initial step was to determine whether $^{125}$I-K16 became associated with the heavy or light chain of GPIIb. $^{125}$I-K16 was cross-linked to thrombin stimulated platelets. Radioactive bands of the GPIIb:K16 complexes were excised from gels run under nonreducing conditions, extracted, and rerun on gels under reducing conditions. Samples were then transferred from the gel onto a PVDF membrane and probed by immunoblotting with the antibodies or subjected to autoradiography. Two previously described anti-peptide antibodies were used for immunoblotting: antibodies raised to the 17 amino acid peptide sequence located at the carboxy-terminus of the heavy chain of GPIIb (anti-V43), and antibodies raised to the 13 amino acid peptide sequence located at the amino-terminus of the light chain of GPIIb (anti-V41). Loftus et al., *J. Biol. Chem.*, 263:11025-28 (1988). The immunoblots developed with these two antibodies (FIG. 3) clearly indicate that, after crosslinking to K16, GPIIb could still be reduced into its heavy and light chain constituents. The autoradiogram of the sample indicated that all the detectable radioactivity migrated in the position of the heavy chain. When the regions of the gels containing the light and heavy chains were excised from the gel and counted, <2% of the radioactivity was in the position of light chain and 98% in the position of the heavy chain. When the GPIIb:K16 extract was run on a second gel but under nonreducing conditions, the intensity of the radioactive band was similar to that observed in the GPIIb heavy chain under reducing conditions (see FIG. 3), providing a control for the recovery of radioactivity in the second gel. When the second gel was of a lower acrylamide concentration (7.5%), differences in the migration under reducing (Rf=0.32) and nonreducing conditions (Rf=0.28) of the labeled GPIIb heavy chain and intact GPIIb, respectively, were clearly discernible.

D. Fragmentation of GPIIb to Identify the Site of Ligand Binding

To localize the K16 crosslinking site within the GPIIb heavy chain, an immunochemical mapping approach was employed using the site-specific monoclonal antibody, PMI-1. This antibody recognizes the extreme carboxy-terminal ten amino acids of the GPIIb heavy chain. Loftus et al., *Proc. Natl. Acad. Sci. USA*, 84:7114-18 (1987). The GPIIb heavy chain:K16 complex was extracted from gels run under reducing conditions according to Example 1C and subjected to short-term proteolysis with chymotrypsin. About 10 ug of extracted GPIIb heavy chain:K16 complex was digested with 5 ug of alpha chymotrypsin for 10 minutes at 22° C. The digested material was then subjected to electrophoresis and immunoblotted using PMI-1 (FIG. 4) according to the methods of Example 1C. Within the partial digest, PMI-1 immunoreacted with a major fragment migrating at 60 kDa as well as two lower molecular weight fragments at 32 and 20 kDa (FIG. 4, lane 2). An autoradiogram of the transfer membrane was prepared also according to Example 1C and indicated that the 60 kDa fragment immunoreacting with PMI-1 was not radioactive (FIG. 4, lane 4). Instead, three lower molecular weight fragments were detected, and these did not align with any of the PMI-1 positive fragments. These results indicated that the 60 kDa region of GPIIb extending toward the amino-terminus from the extreme carboxy-terminus of the heavy chain does not contain the K16 crosslinking site. Conversely, these data suggest that the crosslinking site must reside within the amino-terminal half of the GPIIb heavy chain.

Figure 5:
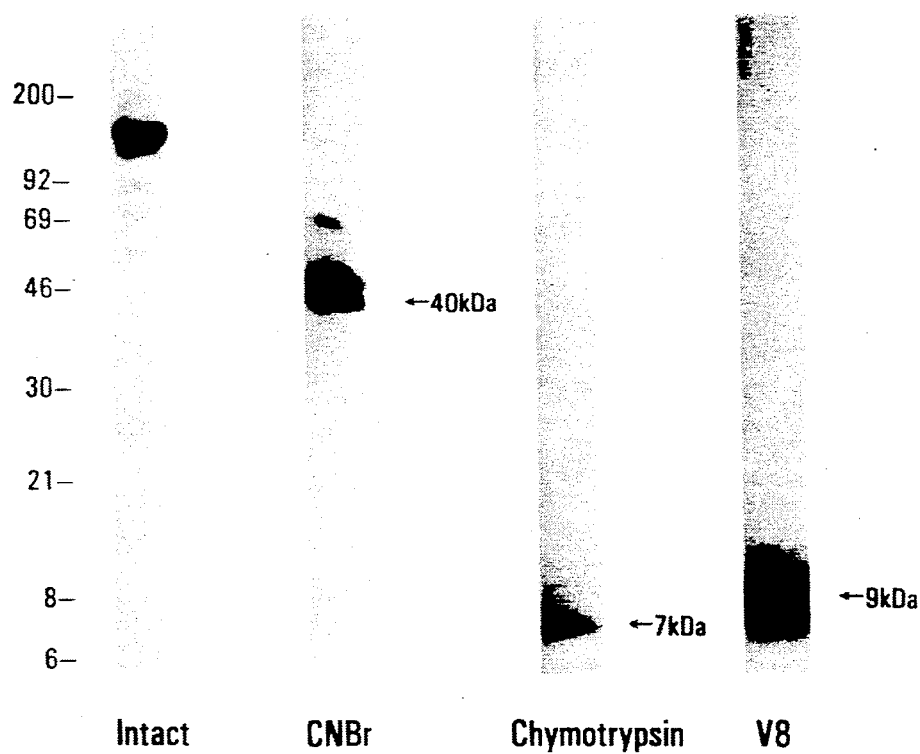

To further locate the K16 crosslinking site, the GPIIb:K16 complex, isolated from SDS-PAGE gels, was subjected to cleavage with cyanogen bromide (CNBr). Upon re-electrophoresis and gel transfer, a major 40 kDa radioactive fragment was consistently observed (FIG. 5). The radioactive fragment was extracted from the SDS-PAGE gel and subjected to $NH_2$-terminal sequence analysis in an Applied Biosystem Model 475A gas-phase sequenator. The results of sequencing the 40 kDa fragment showed that an unambiguous sequence was obtained for 14 cycles. This sequence (FIG. 5) corresponds precisely to the amino-terminal sequence of the GPIIb heavy chain. Similar analyses were performed on two additional preparations of the radioactive CNBr fragment and, in each case, a sequence corresponding to the amino-terminus of GPIIb was obtained. Control experiments were performed which indicated that GPIIb was not sensitive to formic acid cleavage under the conditions used in the CNBr reaction, restricting the CNBr cleavage sites to the methionyl residues of the protein. The first three methionyl residues are located at positions 285, 314 and 489 of GPIIb. See FIGS. 1-1 through 1-9 for amino acid residue position numbers used herein. CNBr cleavage at either of the first two sites would yield a fragment within the 30-40 kDa range (as there are two potential Asn-linked glycosylation sites within this region, precise molecular weights cannot be calculated), compatible with the 40 kDa fragment observed. CNBr cleavage at the third methionyl residue, on the other hand, would yield a fragment of $\geq 54$ kDa. Therefore, the K16 crosslinking site appears to be restricted to a discrete region within the first 314 amino acid residues of GPIIb. Occasionally a radioactive doublet was observed in the CNBr digest, with the higher band having an estimated molecular weight of 54 kDa. This second band is apparent in the CNBr digest in FIG. 5. The amino-terminal sequence of this upper band was also determined and corresponded to the amino-terminal sequences of GPIIb at each of the 10 positions determined. This fragment, therefore, must arise from CNBr cleavage at the methionyl residue at position 489. Together, the radioactivity within these two fragments accounted for 88% of the radioactivity applied to the gel shown in FIG. 5.

A limit digest of the GPIIb heavy chain:K16 complex with chromotrypsin yielded a single 7 kDa radioactive fragment (FIG. 5). Of the radioactivity within the GPIIb:K16 complex, $\geq 90\%$ was recovered in this 7 kDa band. The amino-terminal six residues of this band were determined and corresponded to the GPIIb sequence commencing from residue 294. Sequence analyses of three separate preparations of the 7 kDa fragment yielded at least the three residue sequence AVT, an amino acid sequence unique to residues 294-296 of GPIIb. A 7 kDa fragment beginning at residue 294 should contain approximately 60 amino acids and terminate in the vicinity of residue 350.

To corroborate this localization, SV8 was used to digest the GPIIb heavy chain:K16 complex. The peptide pattern of this digest was extremely complex; therefor, it was first subjected to HPLC on a C4 column. The radioactive fractions were pooled, electrophoresed on a 10 to 20% gradient gel and transferred to a PVDF membrane. Autoradiography of the transfer revealed a broad band in the 8-9 kDa region (FIG. 5) with 95% of the radioactivity applied to the gel migrating in this position. Amino acid sequencing of this band yielded two discernible sequences. One sequence corresponded to the $NH_2$-terminal sequence of SV8 and presumably was derived from a proteolytic fragment of enzyme which comigrated with the radioactive band. The second sequence obtained could be read for 16 cycles and gave interpretable signals at 13 of the 16 positions. This sequence corresponded to that of GPIIb extending from residue 253. A 9 kDa fragment beginning at residue 253 would contain approximately 80 amino acids and would also terminate in the vicinity of residue 350.

Figure 6:
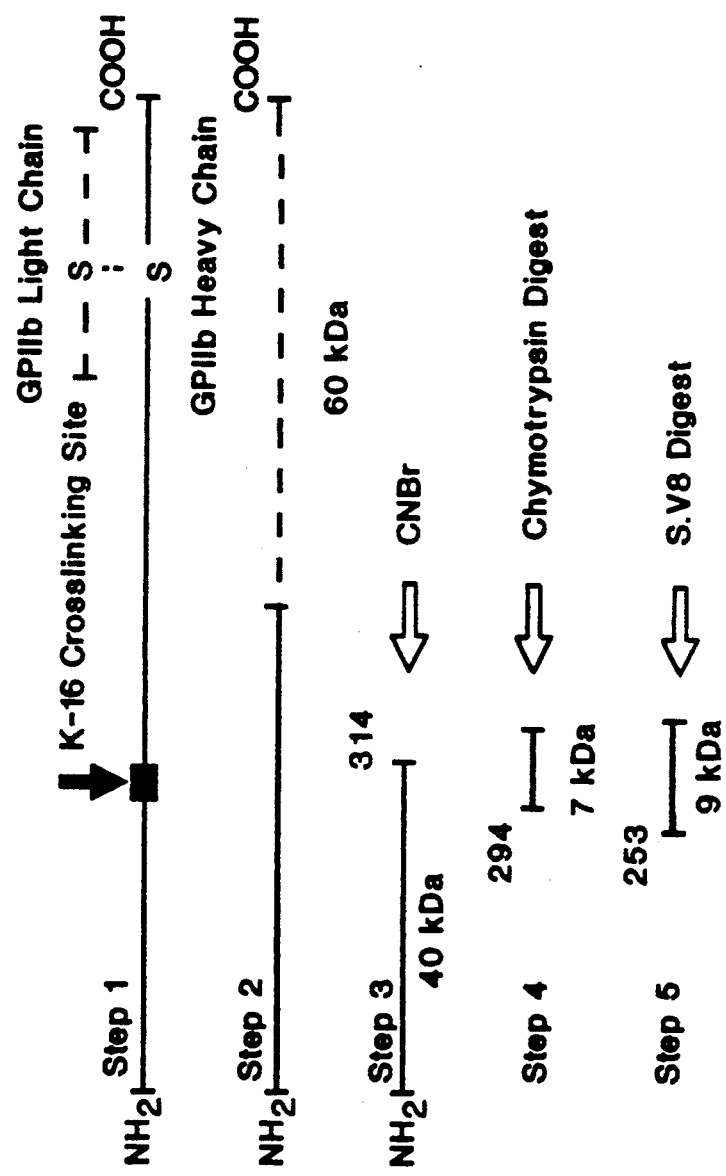

A summary of the data localizing the K16 crosslinking site is schematically illustrated in FIG. 6. Step 1 restricted the crosslinking site to the heavy chain region of GPIIb. Step 2 indicated that the site resided in the amino-terminal one-half of the GPIIb heavy chain based upon the absence of the PMI-1 epitope in a 60 kDa chymotryptic fragment. Step 3 further narrowed the site to the amino-terminal one-third of the subunit based upon the presence of the crosslinked peptide in a 40 kDa CNBr fragment beginning at residue 1 of GPIIb. The methionyl residues at positions 285 or 314 are the two alternative sites for the carboxy-terminus of the 40 kDa fragment. Step 4 confined the crosslinking site to a 7 kDa chymotryptic fragment extending from residue 294. This result establishes that the radioactive CNBr derived fragment must terminate at 314 rather than 285 and places the K16 crosslinking site within a stretch of 21 amino acids. Step 5 established that the crosslinking site resided within the 9 kDa SV8 fragment beginning at residue 253. This fragment is predicted to terminate in the vicinity of residue 350. As the 294–314 region is contained within the SV8 fragment, step 5 provides corroborating evidence for the localization of the K16 crosslinking site deduced from step 4.

The sequence of the 21 amino acid stretch of GPIIb containing the gamma chain crosslinking site is indicated in Table 1 has the same amino acid residue sequence as polypeptide p1 and represents a portion of the fibrinogen-binding region of GPIIb.

The sequence of the gamma chain crosslinking site in GPIIb was optimally aligned with the sequences determined for other alpha subunits of human Integrins, and that alignment is shown in Table 1. A high conservation of primary structure is evident. The sequence identity of this region of GPIIb ranges from 48% for the alpha subunit of Mac-1 to 81% for the alpha subunit of VLA-5, the fibronectin receptor. The overall identity of the entire GPIIb to these other alpha subunits ranges from 22–38%. Such selective conservation of structure favors a role for this region in receptor function. Because of this conservation, this region on the alpha subunits of human Integrins is considered to be "homologous" to the fibrinogen-binding region of GPIIb, and therefor the region is designated herein as the ligand-binding region of the alpha subunit of Integrin.

Insofar as the ligand-binding region was identified by chemical crosslinking to proteolytic fragments, it is believed that the precise boundaries of the ligand-binding site can vary by as much as about 5 to 15 amino acid residues. Therefore the site, for convenience, will be referred to herein as a ligand-binding region on the alpha Integrin subunit, and on GPIIb-IIIa that region encompasses residues from about position 290 to about position 320.

2. Polypeptide Synthesis

The polypeptides shown in Table 2, that correspond to the identified ligand-binding region of an alpha subunit of Integrin, were synthesized using the classical solid-phase technique described by Merrifield, *Adv. Enzymol.*, 32:221–96, (1969) as adapted for use with a model 430 automated peptide synthesizer (Applied Biosystems, Foster City, Ca.). If the polypeptides are to be used for immunizations to prepare polyclonal or monoclonal antibodies, the polypeptides are synthesized with an additional Cys—Gly—Gly (CGG) tripeptide (not shown in Table 2) as a linker attached between the amino terminus of each polypeptide and the carboxy terminal glycine of the tripeptide, to allow for thiol coupling of the polypeptide to a carrier protein. Prepared polypeptide resins were cleaved by hydrogen fluoride, extracted and analyzed for purity by high-performance liquid chromatography (HPLC) using a reverse-phase C18 column manufactured by Waters Associates, Milford, Ma. Polypeptides p3–p9, and the polypeptides shown in Table 3 are also prepared by the above procedure.

3. Inhibition of Platelet Aggregation by Polypeptides

Sixty milliliters (ml) of whole human blood was collected in 5 ml of ACD (0.065 M citric acid, 0.085 M sodium citrate, 2% dextrose) containing hirudin (Sigma Chemical Co., St. Louis, Mo.) at a final concentration of 0.06 units per milliliter (U/ml) and centrifuged for 15 minutes at 120xg. The resulting supernatant, designated platelet rich plasma (PRP), was recovered.

Two hundred ul of the platelet rich plasma (PRP) were admixed with 190 ul Tyrode's buffer containing BSA and dextrose (each at 1 mg/ml), 1 mM $Ca^{2+}$, 300 mM fibrinogen, and polypeptide p1 prepared in Example 2 and added in varying amounts as indicated in Table 4. The control peptide used is residues 461–471 of GPIIb and is representative of 30 GPIIb-IIIa peptides tested. Ten ul of ADP (80 uM in Tyrode's buffer) were then admixed to stimulate platelet aggregation. The admixture was maintained at 37 degrees C. while changes in light transmission of the admixture were monitored over time using a Dual Sample Aggregation Meter (Model DP-247E, Sienco Inc., Morrison, Co.).

The aggregation meter was calibrated using a solution containing 200 ul PRP and 200 ul Tyrode's buffer to set a low baseline of light transmission at 5 percent for control aggregations and at 10 percent for aggregations in the presence of polypeptide. The upper limit of 100 percent light transmission was uniformly set using a mixture of 100 ml PRP and 300 ul Tyrode's buffer.

The results obtained when measuring platelet aggregation inhibition by polypeptide p1 are shown in Table 4, and are expressed as a percent of light transmission (100%) obtained in the absence of polypeptide when measured about 3 to 4 minutes after ADP was admixed. The results in Table 4 show that polypeptide p1 produced a dose-dependent inhibition of platelet aggregation.

Similar results were obtained when platelets were aggregated in a solution containing 1 mM $Ca^{+2}$ and 300 nM fibrinogen. Additionally, 1 mM p1 produced partial inhibition (ca 40%) of aggregation in the presence of strong agonists such as thrombin (60 milliunits/ml) and collagen (5 μg/ml).

TABLE 4

| INHIBITION OF PLATELET AGGREGATION BY POLYPEPTIDES | | |
|---|---|---|
| Polypeptide Designation | Polypeptide Concentration | Percent Transmission |
| control | 1 mM | 100 |
| none | 0 uM | 100 |
| p1 | 5.0 uM | 86 |
| p1 | 50.0 uM | 67 |
| p1 | 125.0 uM | 48 |
| p1 | 1.25 mM | 10 |

When polypeptide p2 was tested in the above aggregation assay it exhibited a measurable, but lower degree of inhibition of platelet aggregation. Polypeptide p2 was about 80 percent less effective than polypeptide p1 in inhibiting platelet aggregation.

Thus, the results indicate the effective dosages useful to inhibit platelet aggregation and processes involving platelet aggregation, such as thrombus formation, when using polypeptides of the present invention that are derived from the fibrinogen-binding region of GPIIb.

4. Preparation of Polyclonal Antisera

The synthetic polypeptides prepared in Example 2 are first coupled to keyhole limpet hemocyanin (KLH) through the thiol residue present on the cysteine residue linker to form polypeptide-KLH conjugates. Balb/c mice are then immunized with 100 micrograms (ug) of conjugate, first intraperitoneally (IP) in complete Freund's adjuvant, and boosters are given subcutaneously and/or intraperitoneally in incomplete Freund's adjuvant.

After three or more boosters, antisera is collected from the responding mice. The collected antisera contains polyclonal antibody molecules that immunoreact with the immunizing polypeptides, and are suitable for use in the methods disclosed herein.

5. Inhibition of Fibrinogen Binding

The inhibitory activity of polypeptide p1 on platelet binding to fibrinogen was examined with $^{125}$I-fibrinogen. $^{125}$I-fibrinogen (60 nM) was added to ADP (10 μM) stimulated washed platelets. The binding of polypeptide p1, a one amino acid variant of p1 (TDVNGEGRHDL=p1'), and a control peptide to $^{125}$I-fibrinogen was determined at final concentrations of 1.0, 0.5, and 0.05 mM at 22° C. Bound radiolabeled fibrinogen was quantitated and expressed as a percent of fibrinogen bound in the absence of polypeptide. The data presented in Table 5 were obtained when $^{125}$I-fibrinogen was preincubated with p1 for 30 minutes prior to addition of ADP-stimulated platelets with binding measured 10 minutes later. The results clearly show the ability of the p1 residue sequence to inhibit fibrinogen binding.

TABLE 5

INHIBITION OF $^{125}$I-FIBRINOGEN BINDING

| Polypeptide | Concentration | % Inhibition |
|---|---|---|
| p1 | 1.0 mM | 70 |
| p1' | 1.0 mM | 27 |
| control | 1.0 mM | 2 |
| p1 | 0.5 mM | 52 |
| p1' | 0.5 mM | 18 |
| control | 0.5 mM | 2 |
| p1 | 0.05 mM | 2 |
| p1' | 0.05 mM | 2 |
| control | 0.05 mM | 2 |

The control peptides were GPIIb 24-33, 363-374, 430-439, and 530-544.

6. Fibrinogen Binding to Immobilized Polypeptides

Polypeptides p1, p1', and controls were immobilized on 96-well Immulon-2 microtiter plates (Dynatech Laboratories, VA). The peptides were added to the plates and maintained at 4 C for 24 hours after which the plates were washed with Hepes-Tyrode's buffer (pH 7.4) containing Tween-20. The plates were post-coated with 3% BSA for 1 hr. at 37° C. and then washed again. $^{125}$I-fibrinogen (50 μL at 50 nM) was allowed to bind to the peptide-coated wells for 24 hours at 22° C. which were then extensively washed and counted for bound radioactivity. The labeled fibrinogen could be displayed by unlabeled fibrinogen, thereby indicative of saturable binding.

In a further experiment, the specificity of fibrinogen binding to immobilized p1 polypeptide was further probed by simultaneously exposing unlabeled fibrinogen, borine serum albumin (BSA) and thyroglobulin with $^{125}$I-fibrinogen (50 nM) to the immobilized p1. The results are presented in Table 6.

TABLE 6

BINDING OF $^{125}$I-FIBRINOGEN TO IMMOBILIZED PEPTIDES

| Immobilized Polypeptide | Unlabelled Ligand | $^{125}$I-Fibrinogen (cpm × 10$^3$) |
|---|---|---|
| p1 | — | 53 |
| p1' | — | 17 |
| Control | — | 6 |
| p1 | — | 28 |
| p1 | 0.2 μM Fibrinogen | 18 |
| p1 | 0.4 μM Fibrinogen | 15 |
| p1 | 0.8 μM Fibrinogen | 9 |
| p1 | 1.2 μm Fibrinogen | 7 |
| p1 | 1.6 μM Fibrinogen | 6 |
| p1 | 1.2 μM BSA | 25 |
| p1 | 1.5 μM BSA | 24 |
| p1 | 1.2 μM Thyroglobulin | 23 |
| p1 | 1.5 μM | 22 |

Thus, fibrinogen binds to iummobilized p1 much more (10-12 times) than to immobilized control peptides and the binding is specific to fibrinogen.

7. Inhibition of Fibrinogen Binding to Immobilized Polypeptide p1.

The inhibition of fibrinogen binding to immobilized p1 was further characterized with the results presented in Table 7. Thus, albumin and thyroglobulin showed minimal inhibition of $^{125}$I-fibrinogen binding relative to specific-binding fibrinogen. Cation dependence of binding was established in the presence of EDTA (5 mM). Two gamma-chain peptides of fibrinogen (HHLGGAKQAGDV and KYGGHHLGGAHQAGDV) inhibited the interaction of fibrinogen with immobilized p1. Also, a monoclonal antibody (4A5) to the gamma-chain region (Matsueda, G.R., et al. *FASEB J.* 2:6480 (1988)) blocked the interaction. Additionally, RGD-containing peptides (RGDS and YVTAGRGDSPASSK) inhibit fibrinogen binding. These observations are consistent with the hypothesis that RGD gamma-chain peptides interact with the same sites in GPIIb-IIIa.

TABLE 7

INTERACTION OF $^{125}$I-FIBRINOGEN WITH IMMOBILIZED p1 PEPTIDE.

| Inhibitor | Concentration % (μM) | Inhibition of $^{125}$I-fibrinogen binding to p1 |
|---|---|---|
| None | | 0 |
| Fibrinogen | 2 | 82 ± 1.2 |
| Albumin | 2 | 12 ± 4 |
| Thyroglobulin | 2 | 14 ± 4 |
| EDTA | 5000 | 90 ± 8 |
| HHLGGAKQAGDV | 200 | 57 ± 11 |
| KYGGHHLGGAKQAGDV | 200 | 54 ± 12 |
| RGDS | 200 | 52 ± 15 |
| GRGESP | 200 | 16 ± 7 |
| YVTAGRGDSPASSK | 200 | 61 ± 16 |
| 4A5 Mab | 10 | 75 ± 8 |
| Control Mab | 10 | 15 ± 4 |

8. Anti-p1-Antibodies Inhibit Fibrinogen Binding

Antibodies to GPIIb-IIIa were generated by immunizing rabbits with GPIIb-IIIa. Rabbit sera was passed over an affinity column (2mg peptide/ml Sepharose 4B) having immobilized p1 polypeptide and the bound antibody was acid eluted (pH 2.5) from the column. The isolated anti-p1 antibodies reacted with p1 at a 1/1000 dilution but no reaction was observed with other GPIIb-IIIa peptides at 1/10 dilution.

Figure 7A:
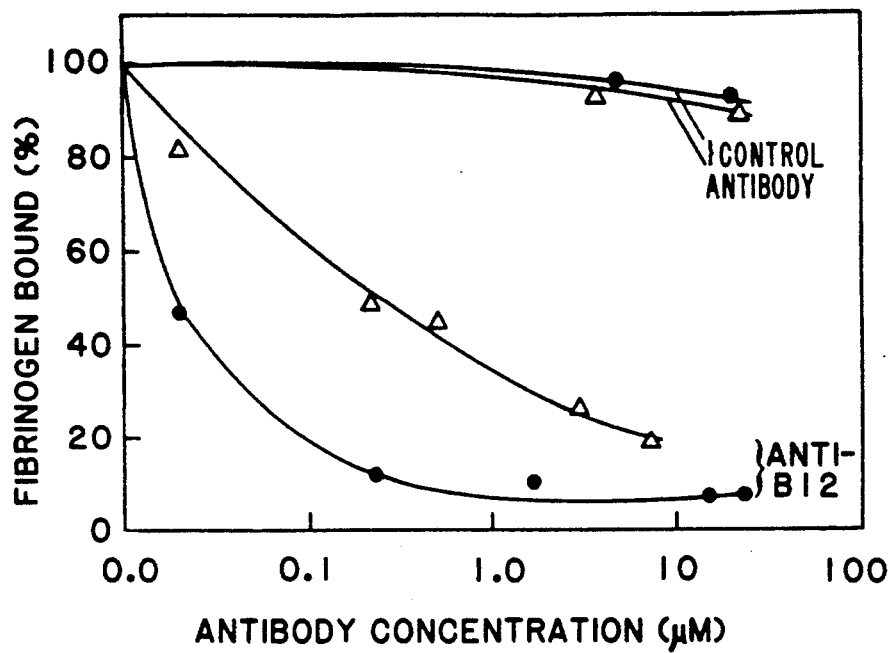
FIG. 7A shows the dependence of $^{125}I$-fibrinogen binding on anti-pl (B12) antibody concentration. pl polypeptide (dark circle) and GPIIb-IIIa (triangle) were immobilized on microtiter plates. The results show selective inhibition of fibrinogen binding by anti-pl antibodies.

As shown in FIG. 7A, the anti-p1 (B12) antibodies isolated exhibit a concentration dependent inhibition of $^{125}$I-fibrinogen (50 nM) binding to p1 (dark circle) and GPIIb-IIIa (triangle) immobilized on microtiter plates for 24h at 22° C. The control antibody was to GPIIb residues 1-13 which was purified using the method employed for the anti-p1 antibodies. The anti-p1 plates were prepared as above and the anti-GPIIb-IIIa plates were prepared by coating microtiter walls with 10 μg/mL GPIIb-IIIa, purified by affinity chromatogrphy on KYGRGDS (Pytela, R., et al., Science, 231:1559-62 (1986)).

Figure 7B:
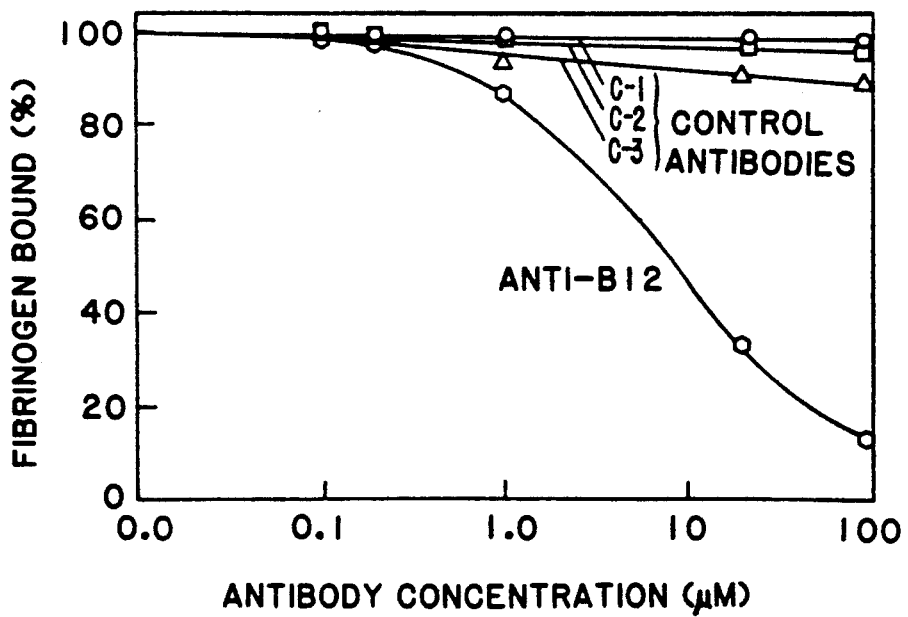
FIG. 7B shows selective inhibition of $^{125}I$-fibrinogen binding to platelets in the presence of anti-pl antibodies.

FIG. 7B shows the effect of anti-p1 (B12) antibodies on $^{125}$I-fibrinogen binding to platelets. $^{125}$I-fibrinogen (60 nM) was incubated with ADP-stimulated washed human platelets ($10^8$/ml) and antibodies for 30 min. at 22° C. The control antibodies were to other regions of GPIIb-IIIa. Antibodies to the p1 polypeptide therefore specifically inhibit fibrinogen binding to platelets.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A polypeptide of ten to about 40 amino acid residues in length including an amino acid residue sequence that corresponds to the ligand binding region sequence of an Integrin alpha subunit, said ligand binding region sequence represented by a formula selected from the group consisting of:
 —TDVNGDGRHDL—,
 —TDINGDDYADV—,
 —VDVDKDTITDV—,
 —VDLNADGFSDL—,
 —TDVNGDGLDDL—,
 —VDVDGDGETEL—,
 —VDVDSNGSTDL—, and
 —VDVDTDGSTDL—.

2. The polypeptide of claim 1, said polypeptide having an amino acid residue sequence selected from the group consisting of:
 TDVNGDGRHDL,
 AVTDVNGDGRHDLLVGAPLYM,
 AATDINGDDYADVFIGAPLFM,
 CSVDVDKDTITDVLLVGAPMYM,
 CAVDLNADGFSDLLVGAPMQS,
 AATDVNGDGLDDLLVGAPLLM,
 CGVDVDGDGETELLLIGAPLFY,
 CSVDVDSNGTDLVLIGAPHYY, or
 CSVDVDTDGSTDLVLIGAPHYY.

3. A nucleotide segment comprising no more than about 2,000 nucleotide base pairs including a sequence defining a structural gene coding for a polypeptide according to claim 1.

4. A polyclonal antibody composition comprising antibody molecules that immunoreact with a polypeptide according to claim 1, but do not immunoreact with an Integrin beta subunit or with a polypeptide whose amino acid residue sequence consists essentially of a sequence that corresponds to the following:
 YELHNNGPGTVNGLHL,
 YELRNNGPSSFSKAML,
 LKVTTGSVPVSMATV,
 TFHVINTGNSMAPNVSV,
 YELINQGPSSISQGVL,
 YQVRIQPSIHDHVIPT,
 YQVSNLGQRSLPISL, or
 YQVSNLGQRSLPISL, or
 YQVNNLGQRDLPVSI.

5. A monoclonal antibody that immunoracts with (a) a polypeptide according to claim 1 and (b) the alpha subunit of an Integrin to which the amino acid residue sequence of said polypeptide corresponds.

6. A monoclonal antibody that immunoreacts with
 (a) GPIIb, and
 (b) a polypeptide having the amino acid residue sequence AVTDVNGDGRHDLLVGAPLYM.

7. A composition that promotes adhesion of cells to a substrate when said composition is immobilized on the substrate comprising a polypeptide of ten to about 40 amino acid residues in length including an amino acid residue sequence that corresponds to the ligand binding region sequence represented by a formula selected from the group consisting of:
 —TDVNGDGRHDL—,
 —TDINGDDYADV—,
 —VDVDKDTITDV—,
 —VDLNADGFSDL—,
 —TDVNGDGLDDL—,
 —VDVDGDGETEL—,
 —VDVDSNGSTDL—, and
 —VDVDTDGSTDL—,
said polypeptide promoting cell adhesion when immobilized on a substrate.

8. The composition of claim 7 comprising a polypeptide having an amino acid residue sequence according to the formula:
 TDVNGDGRHDL,
 AVTDVNGDGRHDLLVGAPLYM,
 AATDINGDDYADVFIGAPLFM,
 CSVDVDKDTITDVLLVGAPMYM,
 CAVDLNADGFSDLLVGAPMQS,
 AATDVNGDGLDDLLVGAPLLM,
 CGVDVDGDGETELLLIGAPLFY,
 CSVDVDSNGSTDLVLIGAPHYY, or
 CSVDVDTDGSTDLVLIGAPHYY,
aid polypeptide promoting cell adhesion when immobilized on a substrate.

* * * * *